(12) United States Patent
Costella et al.

(10) Patent No.: US 11,439,869 B2
(45) Date of Patent: Sep. 13, 2022

(54) POSITIVE EXPIRATORY PRESSURE DEVICE

(71) Applicant: Trudell Medical International, London (CA)

(72) Inventors: Stephen Costella, London (CA); Martin P. Foley, London (CA); Alanna Kirchner, London (CA); Robert Morton, London (CA); Jason Collins, London (CA); Jerry Grychowski, Lake Zurich, IL (US)

(73) Assignee: TRUDELL MEDICAL INTERNATIONAL, London (CA)

( * ) Notice: Subject to any disclaimer, the term of this patent is extended or adjusted under 35 U.S.C. 154(b) by 522 days.

(21) Appl. No.: 15/983,741

(22) Filed: May 18, 2018

(65) Prior Publication Data
US 2019/0001187 A1    Jan. 3, 2019

Related U.S. Application Data

(60) Provisional application No. 62/643,557, filed on Mar. 15, 2018, provisional application No. 62/633,460, (Continued)

(51) Int. Cl.
*A63B 23/18* (2006.01)
*A61M 16/06* (2006.01)
(Continued)

(52) U.S. Cl.
CPC ......... *A63B 23/18* (2013.01); *A61M 16/0006* (2014.02); *A61M 16/06* (2013.01);
(Continued)

(58) Field of Classification Search
CPC .......... A62B 23/18; A62B 7/14; A61M 16/06; A61M 16/0605; A61M 16/208;
(Continued)

(56) References Cited

U.S. PATENT DOCUMENTS 511,780 A    1/1894   Kaplan
669,098 A    3/1901   Overshiner
(Continued)

FOREIGN PATENT DOCUMENTS

CN    103405836    11/2013
EP    0921807      6/1999
(Continued)

OTHER PUBLICATIONS

US 9,433,822 B1, 09/2016, Danford (withdrawn)
(Continued)

*Primary Examiner* — Samchuan C Yao
*Assistant Examiner* — Nathan M Le
(74) *Attorney, Agent, or Firm* — Crowell & Moring LLP

(57) ABSTRACT

A positive exhalation pressure device increases the pressure gradient in the airways, thereby increasing oxygen saturation levels and decreasing the severity of hypoxia. Various embodiments of the device may be inserted into the nasal and/or oral cavities, or configured as mask devices covering the nasal and/or oral cavities. In some embodiments, the resistance of the device may be varied.

23 Claims, 32 Drawing Sheets

Related U.S. Application Data filed on Feb. 21, 2018, provisional application No. 62/572,946, filed on Oct. 16, 2017, provisional application No. 62/541,479, filed on Aug. 4, 2017, provisional application No. 62/508,671, filed on May 19, 2017.

(51) Int. Cl.
  *A61M 16/04* (2006.01)
  *A61M 16/08* (2006.01)
  *A61M 16/00* (2006.01)
  *A61M 16/20* (2006.01)
  *A61M 16/10* (2006.01)

(52) U.S. Cl.
  CPC ...... *A61M 16/0816* (2013.01); *A61M 16/208* (2013.01); *A61M 16/049* (2014.02); *A61M 16/0627* (2014.02); *A61M 16/0666* (2013.01); *A61M 16/0688* (2014.02); *A61M 16/1045* (2013.01); *A61M 2016/0018* (2013.01); *A61M 2016/0027* (2013.01); *A61M 2016/0033* (2013.01); *A61M 2205/0216* (2013.01); *A61M 2205/0272* (2013.01); *A61M 2205/3303* (2013.01); *A61M 2205/3368* (2013.01); *A61M 2205/3375* (2013.01); *A61M 2210/0637* (2013.01); *A61M 2230/202* (2013.01); *A61M 2230/205* (2013.01); *A61M 2230/30* (2013.01); *A61M 2230/42* (2013.01); *A61M 2230/50* (2013.01)

(58) Field of Classification Search
  CPC ... A61M 16/1045; A61M 18/00; A41D 13/11; A41D 13/0512; A41D 13/1107
  See application file for complete search history.

(56) References Cited

U.S. PATENT DOCUMENTS

| | | | |
|---|---|---|---|
| 2,888,012 | A | 5/1959 | Larson |
| 3,097,642 | A | 7/1963 | Russell |
| 3,850,171 | A | 11/1974 | Ball et al. |
| 3,884,223 | A | 5/1975 | Keindl |
| 3,889,671 | A | 6/1975 | Baker |
| 4,601,465 | A * | 7/1986 | Roy .................. A63B 23/18 |
| | | | 128/207.16 |
| 4,881,540 | A | 11/1989 | Vigilia |
| 4,974,829 | A | 12/1990 | Gamow et al. |
| 5,056,756 | A | 10/1991 | Norkey et al. |
| 5,101,819 | A | 11/1992 | Lane |
| 5,425,359 | A | 6/1995 | Liou |
| RE35,339 | E | 10/1996 | Rapoport |
| 5,598,839 | A | 2/1997 | Niles et al. |
| 5,628,308 | A | 5/1997 | Harges, Jr. et al. |
| 5,645,049 | A | 7/1997 | Foley et al. |
| 5,647,345 | A | 7/1997 | Saul |
| 5,730,122 | A | 3/1998 | Lurie |
| 5,848,589 | A | 12/1998 | Welnetz |
| 6,029,667 | A | 2/2000 | Lurie |
| 6,338,340 | B1 | 1/2002 | Finch et al. |
| 6,478,026 | B1 | 11/2002 | Wood |
| 6,511,964 | B2 | 1/2003 | Butler et al. |
| 6,557,549 | B2 | 5/2003 | Schmidt et al. |
| 6,626,179 | B1 | 9/2003 | Pedley |
| 6,722,360 | B2 | 4/2004 | Doshi |
| 6,964,638 | B2 | 11/2005 | Theodoracopulos et al. |
| 7,013,896 | B2 | 3/2006 | Schmidt |
| 7,261,104 | B2 | 8/2007 | Kiefer et al. |
| 7,334,581 | B2 | 2/2008 | Doshi |
| 7,506,649 | B2 | 3/2009 | Doshi et al. |
| 7,559,327 | B2 | 7/2009 | Hernandez |
| 7,735,491 | B2 | 6/2010 | Doshi et al. |
| 7,735,492 | B2 | 6/2010 | Doshi et al. |
| 7,798,148 | B2 | 9/2010 | Doshi et al. |
| 7,806,120 | B2 | 10/2010 | Loomas et al. |
| 7,856,979 | B2 | 12/2010 | Doshi et al. |
| 7,987,852 | B2 | 8/2011 | Doshi et al. |
| 7,992,563 | B2 | 8/2011 | Doshi et al. |
| 7,992,564 | B2 | 8/2011 | Doshi et al. |
| 8,020,700 | B2 | 9/2011 | Doshi et al. |
| 8,026,077 | B2 | 9/2011 | Madden |
| 8,061,357 | B2 | 11/2011 | Pierce et al. |
| 8,215,308 | B2 | 7/2012 | Doshi et al. |
| 8,235,046 | B2 | 8/2012 | Doshi et al. |
| 8,240,309 | B2 | 8/2012 | Doshi et al. |
| 8,281,557 | B2 | 10/2012 | Doshi et al. |
| 8,291,909 | B2 | 10/2012 | Doshi et al. |
| 8,302,606 | B2 | 11/2012 | Doshi et al. |
| 8,302,607 | B2 | 11/2012 | Pierce et al. |
| 8,327,849 | B2 | 12/2012 | Foley et al. |
| 8,365,736 | B2 | 2/2013 | Doshi et al. |
| 8,475,340 | B2 | 7/2013 | Maybaum |
| 8,590,533 | B2 | 11/2013 | Danford |
| 8,646,449 | B2 | 2/2014 | Bowsher |
| 8,690,750 | B2 | 4/2014 | Krueger |
| 8,707,955 | B2 | 8/2014 | Doshi |
| 8,875,711 | B2 | 11/2014 | Sather et al. |
| 8,985,116 | B2 | 3/2015 | Doshi et al. |
| 9,066,933 | B2 | 6/2015 | Wong et al. |
| 9,067,086 | B2 * | 6/2015 | Danford .............. A63B 21/0085 |
| 9,192,796 | B2 | 11/2015 | Patil et al. |
| 9,238,113 | B2 | 1/2016 | Loomas et al. |
| 9,284,287 | B1 | 3/2016 | Kandula |
| 9,309,286 | B2 | 4/2016 | Kayyali |
| 9,326,885 | B2 | 5/2016 | Robitaille |
| 9,333,318 | B2 | 5/2016 | Cragg et al. |
| 9,403,826 | B2 | 8/2016 | Kandula |
| 9,573,885 | B2 | 2/2017 | Pelletier et al. |
| 9,579,540 | B1 * | 2/2017 | Danford .............. A63B 21/0004 |
| 9,615,962 | B2 | 4/2017 | Robitaille |
| 9,643,048 | B1 | 5/2017 | Danford |
| 9,707,444 | B1 | 7/2017 | Danford |
| 9,802,079 | B1 | 10/2017 | Danford |
| 2003/0121520 | A1 | 7/2003 | Parker et al. |
| 2003/0170377 | A1 | 9/2003 | Hammel |
| 2005/0098183 | A1 | 5/2005 | Nash et al. |
| 2006/0254592 | A1 | 11/2006 | Anders et al. |
| 2007/0113849 | A1 * | 5/2007 | Matthews ......... A61M 16/0069 |
| | | | 128/204.22 |
| 2007/0113853 | A1 * | 5/2007 | Pavesi .................... A62B 9/003 |
| | | | 128/205.25 |
| 2008/0083410 | A1 | 4/2008 | Resnick |
| 2008/0142015 | A1 | 6/2008 | Groll |
| 2008/0223370 | A1 | 9/2008 | Kim |
| 2008/0245370 | A1 | 10/2008 | Kobziar et al. |
| 2009/0131490 | A1 | 5/2009 | Swenson |
| 2009/0194100 | A1 | 8/2009 | Minagi |
| 2009/0298747 | A1 | 12/2009 | Shapiro |
| 2010/0024826 | A1 * | 2/2010 | Sullivan, Jr. ........ A41D 13/1146 |
| | | | 128/207.11 |
| 2010/0043788 | A1 | 2/2010 | Fine et al. |
| 2010/0326433 | A1 | 12/2010 | Williams |
| 2011/0005530 | A1 | 1/2011 | Doshi et al. |
| 2011/0100369 | A1 | 5/2011 | Zhang et al. |
| 2012/0088776 | A1 | 4/2012 | Supuran et al. |
| 2012/0201906 | A1 | 8/2012 | Reynolds et al. |
| 2012/0305001 | A1 * | 12/2012 | Tatkov .............. A61M 16/0622 |
| | | | 128/205.25 |
| 2013/0081637 | A1 | 4/2013 | Foley et al. |
| 2013/0102916 | A1 * | 4/2013 | Colbaugh ............ A61B 5/4818 |
| | | | 600/533 |
| 2013/0118498 | A1 * | 5/2013 | Robitaille ......... A61M 16/0006 |
| | | | 128/205.16 |
| 2013/0131028 | A1 | 5/2013 | Snyder et al. |
| 2013/0152930 | A1 | 6/2013 | Votel et al. |
| 2013/0312757 | A1 * | 11/2013 | Cragg ............... A61M 16/0683 |
| | | | 128/205.24 |
| 2013/0319420 | A1 * | 12/2013 | Danford .............. A63B 21/0004 |
| | | | 128/206.21 |
| 2013/0325498 | A1 | 12/2013 | Muza, Jr. et al. |
| 2014/0096768 | A1 | 4/2014 | Lee |

(56) References Cited

U.S. PATENT DOCUMENTS

| | | | |
|---|---|---|---|
| 2014/0134191 A1 | 5/2014 | Weidanz et al. | |
| 2014/0246024 A1 | 9/2014 | Cragg et al. | |
| 2014/0246025 A1 | 9/2014 | Cragg et al. | |
| 2014/0276177 A1* | 9/2014 | Brambilla | A61M 16/0666 |
| | | | 600/543 |
| 2014/0283837 A1 | 9/2014 | Turrisi | |
| 2014/0345623 A1 | 11/2014 | Pierce et al. | |
| 2015/0059758 A1* | 3/2015 | Matila, Jr. | A61M 16/06 |
| | | | 128/205.25 |
| 2015/0087660 A1 | 3/2015 | Kandula | |
| 2015/0225460 A1 | 8/2015 | Fischer et al. | |
| 2015/0231443 A1 | 8/2015 | Halliday | |
| 2015/0245675 A1* | 9/2015 | Chinquee | A61F 9/029 |
| | | | 2/424 |
| 2015/0267695 A1 | 9/2015 | Marsh | |
| 2016/0089553 A1* | 3/2016 | Dickstein | A62B 18/10 |
| | | | 128/202.27 |
| 2016/0128863 A1 | 5/2016 | Loomas et al. | |
| 2016/0129286 A1 | 5/2016 | Danford | |
| 2016/0129287 A1 | 5/2016 | Danford | |
| 2016/0143770 A1 | 5/2016 | Vezina et al. | |
| 2016/0316831 A1* | 11/2016 | Yarahmadi | A41D 23/00 |
| 2016/0361067 A9 | 12/2016 | Cline et al. | |
| 2017/0042909 A1 | 2/2017 | Yin et al. | |
| 2017/0043115 A1 | 2/2017 | Murphy et al. | |
| 2017/0065791 A1 | 3/2017 | Nussbaum et al. | |
| 2017/0144000 A1 | 5/2017 | Danford | |
| 2017/0173281 A1 | 6/2017 | Engelbreth et al. | |
| 2017/0274246 A1 | 9/2017 | Danford | |
| 2019/0060707 A1 | 2/2019 | Verges et al. | |

FOREIGN PATENT DOCUMENTS

| | | |
|---|---|---|
| EP | 1247525 | 10/2002 |
| EP | 1503768 | 2/2005 |
| EP | 2866824 | 5/2015 |
| EP | 2937089 | 10/2015 |
| EP | 3141542 | 3/2017 |
| GB | 2211098 A | 6/1989 |
| WO | WO2004/014352 | 2/2004 |
| WO | WO2009/009829 | 1/2009 |
| WO | WO2009/139925 | 11/2009 |
| WO | WO2010/021941 | 2/2010 |
| WO | WO2012/003390 | 1/2012 |
| WO | WO2012/144938 | 10/2012 |
| WO | WO2013/167994 | 11/2013 |
| WO | WO2014/180239 | 11/2014 |
| WO | WO2015/106678 | 7/2015 |
| WO | WO2015/140125 | 9/2015 |
| WO | WO2016/134032 | 8/2016 |
| WO | WO2016/191791 | 12/2016 |
| WO | WO2016/203400 | 12/2016 |
| WO | WO2016/203401 | 12/2016 |
| WO | WO2017/020068 | 2/2017 |

OTHER PUBLICATIONS

Johnson, Pamela et al.; Non-Invasive Positive Pressure Ventilation during Sleep at 3800m: Relationship to Acute Mountain Sickness and Sleeping Oxyhemoglobin Saturation: National Institute of Health Public Access—Author Manuscript, Feb. 2010 (14 pgs).

Khayat, Rami N. et al.; Cardiorespiratory Effects of Added Dead Space in Patients with Heart Failure and Central Sleep Apnea: www.chestjournal.org CHEST / 123 / 5 / May 2003 (10 pgs).

Launay, J-C et al.; Prevention of Acute Mountain Sickness by Low Positive End-Expiratory Pressure in Field Conditions: www.ncbi.nlm.nih.gov/pubmed/15458016 Scand J Work Environ Health 2004 (6 pgs).

Lipman, Grant S. et al.; Study Looking at End Expiratory Pressure for Altitude Illness Decrease (Sleep-Aid): High Altitude Medicine & Biology, vol. 16, No. 2, 2015 (8 pgs).

Lovis, A. et al.; Effect of Added Dead Space on Sleep Disordered Breathing at High Altitude: www.elsevier.com/locate/sleep Sleep Medicine, 13, 2012 (5 pgs).

Nespoulet, Hugo et al.; Positive Expiratory Pressure Improves Oxygenation in Healthy Subjects Exposed to Hypoxia: PLOS ONE | www.plosone.org, Dec. 2013, vol. 8, Issue 12 (11 pgs).

Patz, Michael Dandy et al.; Dead Space Mask Eliminates Central Apnea at Altitude: High Altitude Medicine & Biology, vol. 14, No. 2, 2013 (8 pgs).

Savourey, Gustave et al.; Positive End Expiratory Pressure as a Method for Preventing Acute Mountain Sickness: Eur J Appl Physiol 1998 (2 pgs).

Schoene, Robert B. et al.; High Altitude Pulmonary Edema and Exercise at 4,400 Meters on Mount McKinley—Effect of Expiratory Positive Airway Pressure (4 pgs).

Xie, Ailiang et al.; Effects of Inhaled $CO_2$ and Added Dead Space on Idiopathic Central Sleep Apnea: The American Physiological Society www.physiology.org/journal/jappl, Mar. 2019 (9 pgs).

International Search Report and Written Opinion for International Application No. PCT/IB2018/053527 dated Sep. 5, 2018 (13 pages).

European Search Report for European Application No. EP 18 80 1926 dated Feb. 10, 2021 (8 pgs).

\* cited by examiner

FIG. 1A
FIG. 1B
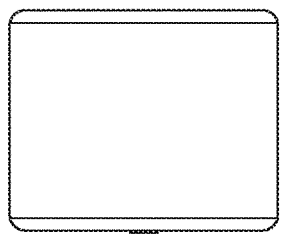
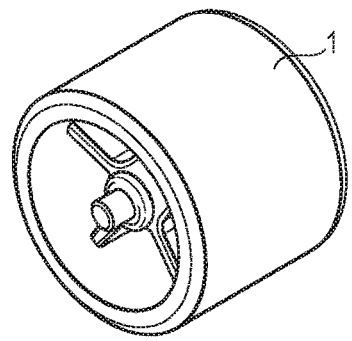
FIG. 1C
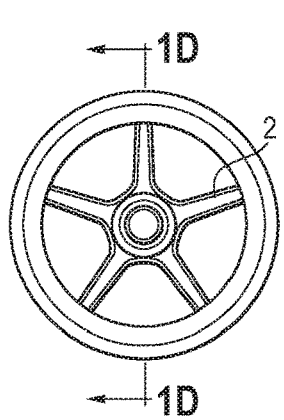
FIG. 1D
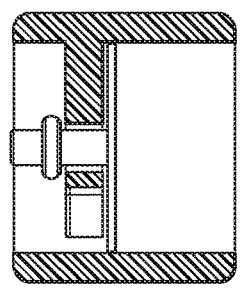
FIG. 1E
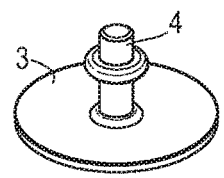
FIG. 2A
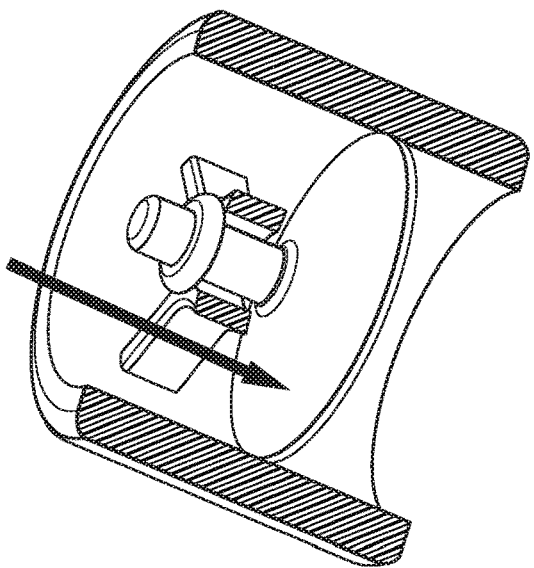
FIG. 2B
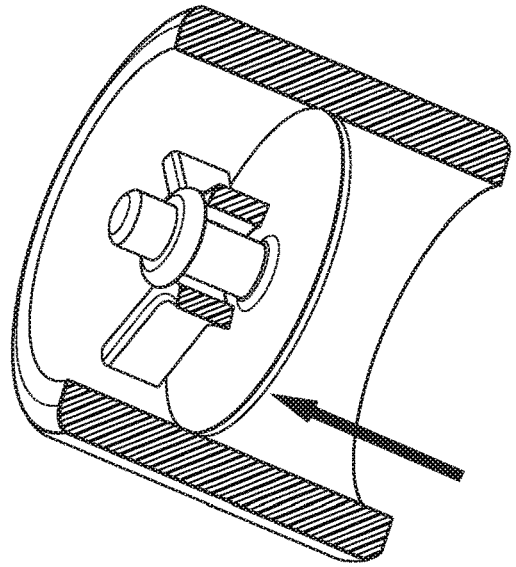

FIG. 18A
FIG. 18B
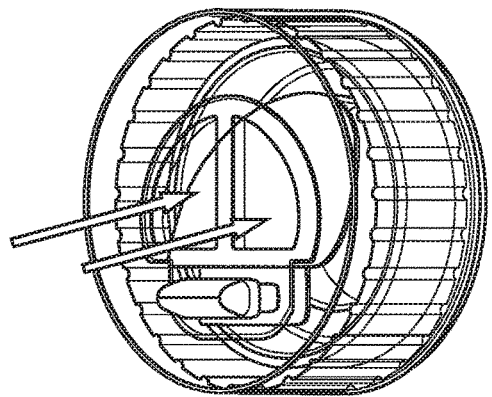
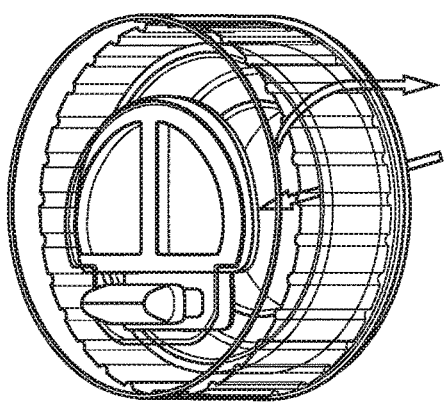
FIG. 19A
FIG. 19B
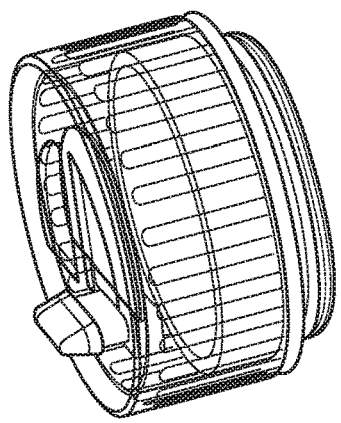
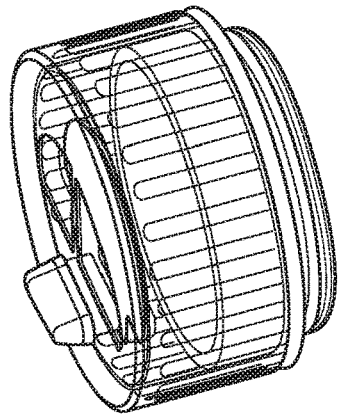
FIG. 19C
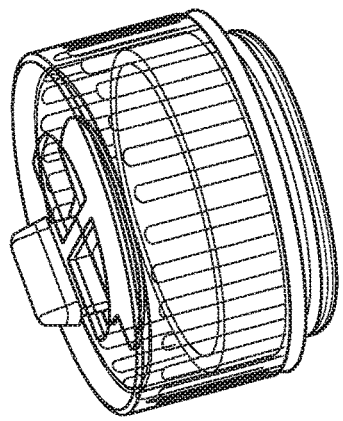

FIG. 45

| Variable | Calculation | Threshold |
|---|---|---|
| SpO2 | Average SpO2 | - |
| | Risk of AMS | ↓ by 4.9% within 30mins OR ↓ by 4.9% compared to average at altitude |
| | Risk of HAPE | ↓ by 10-20% compared to average at altitude |
| EtO2 | Average EtO2 | - |
| EtCO2 | Average EtCO2 | - |
| | Estimate PaCO2 | - |
| | Apnea-Hypopnea Index (AHI) | > 5 apneas per hour during sleep |
| Pressure | Pmin, Pmax, PEEP, Pavg-Risk of barotrauma | > 10cmH2O exhalation pressure |
| | Apnea-Hypopnea Index (AHI) | > 5 apneas per hour during sleep |
| Flow | Minute ventilation | Slow, deep breaths (threshold dependent on user's breathing pattern) |
| | Respiratory rate | |
| Pulse Rate | Average Pulse Rate | 220-age |
| Blood pressure | Average blood pressure | Normal: <120/80 Pre-hypertension: 120/80 - 139/89 Stage 1 hypertension: 140/90 - 159/99 Stage 2 hypertension: ≥ 160/100 |
| Body temperature | Average body temperature | Hypothermia: <35.0°C (95.0°F) OR Fever or hypothermia: >37.5°C (99.5°F) OR Hyperpyrexia: >40.0°C (104.0°F) |
| Cerebral Blood Flow | Average CBF | Peaks in 2-3 days |
| Supplemental oxygen usage | Amount remaining in tank | <10% |
| Barometric Pressure | Altitude | - |
| Barometric Pressure | Risk of AMS | > 500m ascent/day |
| | Time at altitude | Symptom onset after 3 days - not AMS |

FIG. 46

| Altitude (m) | Barometric P (mmHg) | Average PaO2 (mmHg) | Average SaO2 (%) | Average PaCO2 (mmHg) |
|---|---|---|---|---|
| 0 | 760 | 90-100 | 97-99 | 38-42 |
| 1610 | 623 | 65-80 | 93-97 | 32-42 |
| 2440 | 564 | 45-70 | 88-95 | 31-36 |
| 3660 | 483 | 42-53 | 80-89 | 24-34 |
| 5330 | 388 | 38-50 | 65-81 | 22-30 |
| 8840 | 253 | 28-32 | 54-62 | 10-14 |

POSITIVE EXPIRATORY PRESSURE DEVICE

This application claims the benefit of U.S. Provisional Application No. 62/643,557, filed Mar. 15, 2018, U.S. Provisional Application No. 62/633,460, filed Feb. 21, 2018, U.S. Provisional Application No. 62/572,946, filed Oct. 16, 2017, U.S. Provisional Application No. 62/541,479, filed Aug. 4, 2017, and U.S. Provisional Application No. 62/508,671, filed May 19, 2017, the entire disclosures of which are hereby incorporated herein by reference.

BACKGROUND

Oxygen plays a critical role in breathing and metabolism of living organisms. When sufficient oxygen is present in cells, approximately 34 adenosine triphosphate (ATP) molecules are produced via aerobic respiration to use as energy within the body. In the absence of oxygen, cells are forced to produce energy through anaerobic processes, yielding significantly less energy (approximately 2 ATP molecules). Oxygen reaches the lungs via ventilation, diffuses into capillaries and binds to hemoglobin in the blood, where it is transported to tissues through the circulatory system. The amount of oxygen-bound hemoglobin relative to the total amount of hemoglobin in the blood is referred to as oxygen saturation.

Oxygen saturation levels are often referenced as the fifth vital sign, providing valuable insight on the health of an individual. In healthy individuals at sea level, the body maintains a relatively stable level of oxygen saturation around 97-99%. When the body does not have enough oxygen, hypoxemia (low oxygen in the blood) and hypoxia (low oxygen in tissues) will occur. Causes of hypoxia include, but are not limited to, lung diseases such as chronic obstructive pulmonary disease, emphysema, bronchitis, interstitial lung disease, fibrosing alveolitis, acute respiratory distress syndrome, pneumonia, pulmonary edema and acute asthma attacks, strong pain medications that alter ventilation (i.e. certain narcotics and anesthetics), lung abscess, tuberculosis, lymphoma, sarcoidosis, anemia, cyanide poisoning, congenital heart defects, congenital heart disease, pneumothorax, pulmonary edema, pulmonary embolism, extreme obesity, suppressed respiratory signaling due to drug/alcohol toxicity or a brain injury, extreme exercise, sleep apnea, hypoventilation and high altitude.

Hikers, skiers, mountaineers and other adventure travelers who visit high altitudes have an increased risk of developing acute mountain sickness (AMS) as altitude increases and the amount of oxygen available to the body decreases. Onset of AMS symptoms may occur at approximately 2,500 m (8,000 ft), at which roughly 25% of people will develop symptoms of AMS. As altitude increases, the risk of developing AMS increases, with 100% of people acquiring symptoms above 5,000 m (16,000 ft). Current prevention methods for AMS, such as acetazolamide, staged ascent profiles or intermittent hypoxia training, pre-acclimatization, *Ginkgo biloba*, supplemental oxygen, allowing time to rest and minimize activities, pursed lip breathing and adequate hydration, aim to increase oxygen saturation levels in some form. These methods and devices have various drawbacks, including for example and without limitation, pre-ascent planning and training, portaging of supplemental oxygen containers and administration devices, and/or acquisition and ingestion of various supplements and/or medications. The disclosed devices address these various limitations in current practices for increasing oxygen saturation levels.

Positive airway pressure (PAP) such as continuous positive airway pressure (CPAP), variable or bi-level positive airway pressure (VPAP or BPAP), automatic positive airway pressure (APAP) or expiratory positive airway pressure (EPAP, also referred to as positive exhalation/expiratory pressure or PEP), are often used as a treatment for sleep apnea and respiratory diseases such as chronic obstructive pulmonary disease and asthma. Positive airway pressure can be used for individuals not acclimatized to altitude to improve oxygen saturation levels and decrease the risk of AMS. Current limitations on portability, comfort and energy requirements warrant the need for an improved solution for high altitude travelers, which may transferrable to other applications warranting an increase in oxygen saturation.

SUMMARY

A device provides positive exhalation/expiratory pressure (PEP) to increase the pressure gradient in the airways, thereby increasing oxygen saturation levels and decreasing the severity of hypoxia. The device improves upon limitations associated with current methods for preventing acute mountain sickness (AMS), which may include but are not limited to side effects associated with pharmaceuticals, increased time spent at incremental altitudes (slower ascent profiles), resources spent prior to travel to acclimatize in simulated environment, lack of evidence to support effectiveness, lack of portability and supply of supplemental oxygen, technique and thought required to practice pursed lip breathing and requirement to minimize exertion. For applications where oxygen saturation levels are decreased, the disclosed device improves portability, effectiveness and efficiencies to decrease hypoxia.

The disclosed devices provide PEP by adding resistance in series with the nasal and/or oral passageways, and combinations thereof, to provide an exhalation resistance greater than inhalation resistance. In one embodiment, the device includes a valve biased to inhalation and a restricted orifice or positive end-expiratory pressure (PEEP) valve for exhalation. The device may include multiple settings and allow for incremental resistances on exhalation to accommodate various individuals and allow for flexibility and improvements in technique. Another embodiment of the device may block exhalation through the mouth almost entirely, forcing exhalation through the nose with a portion of the device acting as a clip on the outside of the nose to decrease the available nostril size.

Embodiments intended for oral breathing include a portion of the device that fits snugly over a portion of the teeth, with the resistive load residing internal or external to the mouth. Embodiments intended for nasal breathing include a portion of the device that secures and seals within each nostril, or across the front of the nostril openings, with the resistive load residing internal or external to the nasal passage. Embodiments intended for oral and nasal breathing may include a combination of both oral and nasal breathing embodiments discussed above. In one alternate embodiment, the desired resistance may be provided by an electronically controlled resistive load, with programmed settings or utilizing an algorithm to provide a suitable resistance dependent on the user's breathing profile.

Pursed lip breathing (PLB) is a technique commonly used to help improve oxygen saturation, as it involves an individual consciously exhaling through tightly pressed lips to increase pressure on exhalation, effectively providing PEP when done properly. PLB effectiveness may be limited as it requires conscious effort and well understood technique. In one embodiment, the device promotes PLB by monitoring breathing patterns and informing the user when their technique is insufficient via some form of notification, for example a smart phone, watch or other communication device. The communication device may be worn on the body and may be adhered via an adhesive, band, chain, hook, or other fastening component. Notifications may be audible, visual, haptic or a combination thereof.

Aside from the value of PEP in increasing oxygen saturation levels, embodiments of the device may include additional features that add value to users. Such features may include any one of the following or any combination thereof.

Integrated monitoring capabilities with the ability to keep track of the individual wearing, or otherwise associated with, the device and share data with others, for example with sensors that collect data such as oxygen saturation levels (i.e. pulse oximeter), respiration rate, inhalation/exhalation pressure, inhalation/exhalation flow, pulse rate, blood pressure, temperature, number of steps, calories, distance traveled, position (i.e. GPS), altitude, barometric pressure, hydration level, nutrition level, quality of sleep, blood lactate levels, supplemental oxygen usage, exhaled $CO_2$ content, etc.

Reminders to do common tasks associated with activity, such as hydrate, intake nutrition, apply sunscreen, monitor for AMS, take medications, take moments to relax, weather updates, directions, alarms, etc.

Integrated communication component, with audible (i.e. whistle) or visual component used to deter wildlife, communicate with others in group, send out distress call, etc.

Integrated camera to document and take photos, with or without image processing capabilities to perform algorithms including but not limited to facial recognition to determine health status of other individuals, some form of template matching to determine species of plants or animals, location identification, medication identification etc.

Powered via solar energy, energy from user's breath, lactate in user's sweat, movement of user or other form of sustainable energy.

Designed in a material that has a pleasant taste or smell, to enhance comfort and experience wearing the device.

Adapter to connect with supplemental oxygen to further improve oxygen saturation levels.

Combined with sunglasses to protect eyes from UV rays at altitude and aid in securing device to nose.

Portion of device infused with or producing substance that deters insects or other pests without harm to the user, such as citronella, lemon eucalyptus, neem oil, bog-myrtle, etc.

Designed in a material that when disposed of with other waste (i.e. sanitary products, feces, etc.), the material adds a more pleasant aroma or aims to eliminate unpleasant odors.

Designed and integrated in a neck warmer or balaclava used to keep warm and apply PEP with restrictive load as described herein or with a load created with the same material as the neck warmer.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

BRIEF DESCRIPTION OF THE DRAWINGS

FIGS. 1A-E are top, isometric, front, cross-sectional views of one embodiment of the device, shown together with one embodiment of a valve used therein.

FIGS. 2A and B are partial cross-sectional views of the device shown in FIG. 1B during inhalation and exhalation respectively.

FIGS. 18A and B are isometric views of the device shown in FIG. 17B during inhalation and exhalation respectively.

FIGS. 19A-C are isometric views of the device shown in FIG. 17B with a variable resistance dial shown in different positions ranging from a lowest to highest pressure setting.

FIG. 45 is a table showing sensor variables with associated calculations and thresholds.

FIG. 46 is a table showing average values of different parameters at different altitudes.

DETAILED DESCRIPTION OF THE PRESENTLY PREFERRED EMBODIMENTS

Figure 3A:
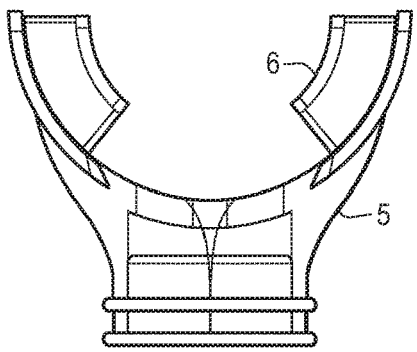
FIG. 3A-D are top, isometric, front, and cross-sectional views of another embodiment of the device.
Figure 3B:
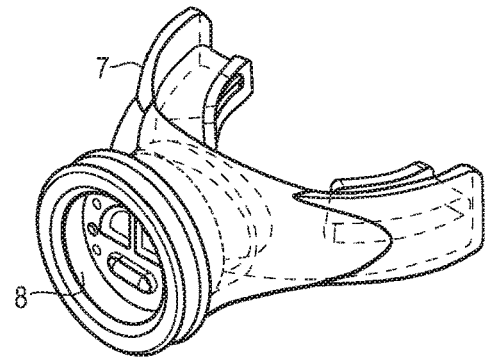
Figure 3C:
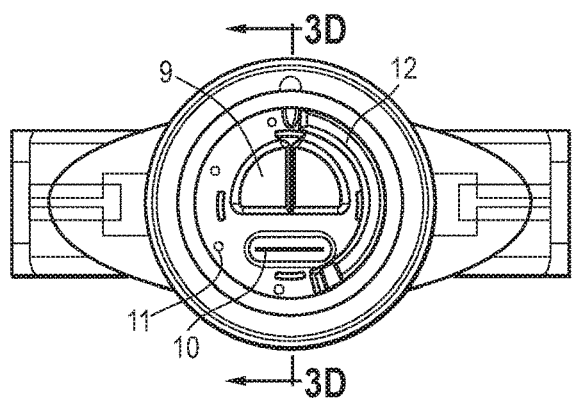
Figure 3D:
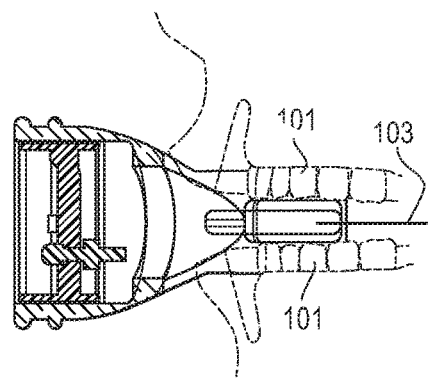

Referring to the drawings, various nasal inserts, nasal insert assemblies and nasal plugs are shown. The phrase "nasal insert," "nasal insert assembly" and "nasal plug" refer to a nasal insert configured to interface with or cover one or both nasal cavities of the user, or in a cavity formed in the user's tracheotomy.

The terms "longitudinal" and "axial" as used herein relates to a length or lengthwise direction, including for example generally the direction of flow of fluids through the nasal inserts and assemblies. The term "lateral" and variations thereof refer to a sideways direction. The terms "top" and "bottom" are intended to indicate directions when viewing the nasal insert when positioned for insertion into the nasal cavity of the user, with the "top" end thereof being inserted first. However, it should be understood that a user can use the nasal insert and assembly when the user is in any number of positions, including but not limited to an upright position (seated or standing) or horizontal position (whether lying sideways, prone or supine).

It should be understood that the term "plurality," as used herein, means two or more. The term "coupled" means connected to or engaged with, whether directly or indirectly, for example with an intervening member, and does not require the engagement to be fixed or permanent, although it may be fixed or permanent. The term "transverse" means extending across an axis, including without limitation substantially perpendicular to an axis. It should be understood that the use of numerical terms "first," "second," "third," etc., as used herein does not refer to any particular sequence or order of components; for example "first" and "second" members may refer to any sequence of such members, and is not limited to the first and second members of a particular configuration unless otherwise specified.

Figure 16A:
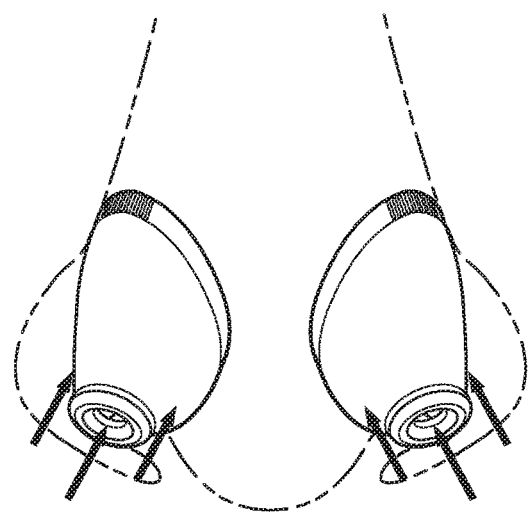
FIGS. 16A and B are isometric views of pairs of the device shown in FIG. 15B during inhalation and exhalation respectively.

The device disclosed in FIGS. 1A-E is intended to be inserted in a person's nostril, with the nasal plug 1 securing and sealing within each nostril. The nasal plug 1 is a rigid housing with an opening on either end creating a channel between atmosphere and the nasal cavity. In one embodiment, the rigid housing is cylindrical, with an annular side wall defining a central passageway/channel having a longitudinal axis. The opposite ends of the annular side wall have an outer curved shoulder or chamfer. In between the openings at each end of the housing on the nasal plug 1 is a frame, configured as a plurality of ribs 2, that create a housing or support structure for the valve 3, which is held in place by a valve post 4 engaging a central hub of the frame. The ribs/frame define a valve seat for the valve and extend across the central passageway. The valve type may be but is not limited to an umbrella valve, ball check valve, duckbill valve, butterfly valve, flap valve, or any other valve reasonably assumed to be used for limiting flow to one direction with low resistance. FIGS. 2A and B show the mechanics of the device during inhalation (FIG. 2A), with the valve 3 open away from the frame and valve seat to allow flow through the channel into a person's nasal passage during inhalation. During exhalation (FIG. 2B), the valve 3 closes or seats against the ribs 2 and flexes slightly in the opposing direction between ribs 2 to create small channels for resisted exhalation flow. During use, the device includes two nasal plugs 1, one for each nostril, as shown for the embodiment of FIGS. 16A and B. The individual nasal plugs 1 may be fastened together with some form of a rigid or flexible connector or tether. Additionally, the nasal plugs 1 may be encased with a flexible material that conforms to a person's nostril shape to improve comfort and obtain a more reliable seal. Various features of a nasal cannula, including a housing, valves and tether, are disclosed in U.S. Pub. No. 2013/0081637 and U.S. Pat. No. 9,615,962, the entire disclosures of which are hereby incorporated herein by reference.

Figure 4A:
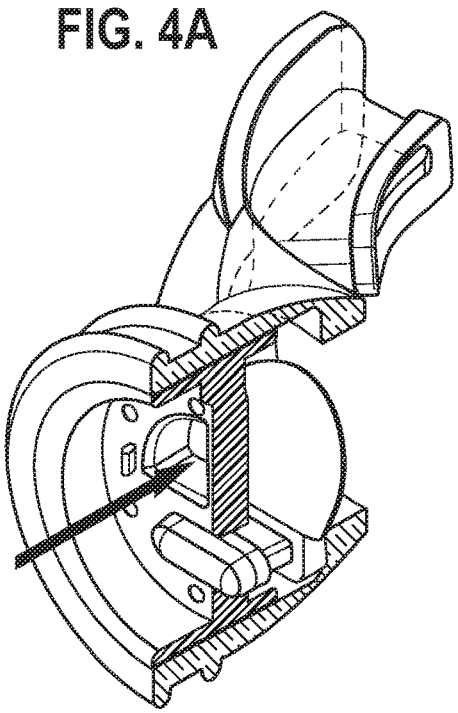
FIGS. 4A and B are partial cross-sectional views of the device shown in FIG. 3B during inhalation and exhalation respectively.
Figure 4B:
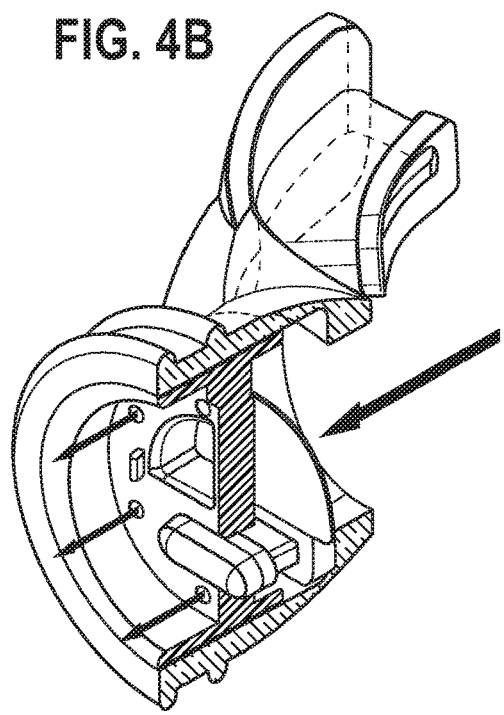
Figure 5A:
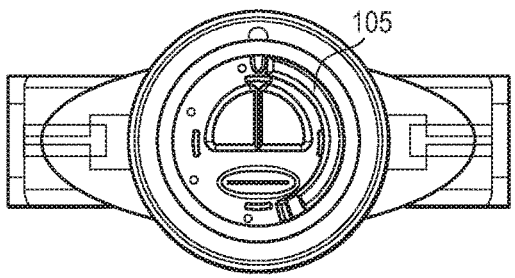
FIGS. 5A-D are front views of the device shown in FIG. 3C with a variable resistance dial shown in different positions ranging from a lowest to highest pressure setting.
Figure 5B:
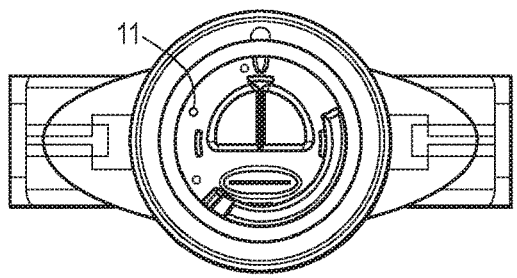
Figure 5C:
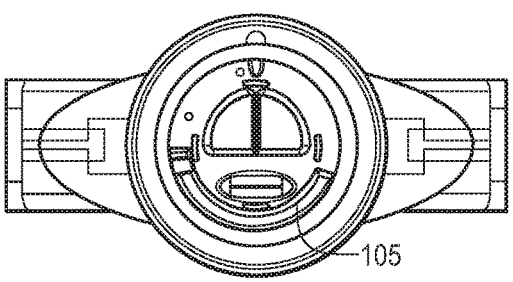
Figure 5D:
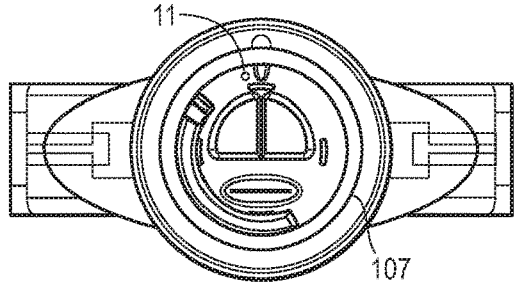
Figure 6A:
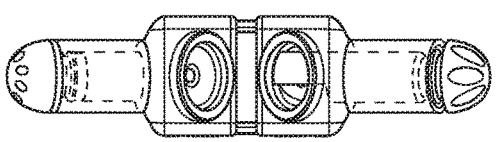
FIGS. 6A-D are top, isometric and front views of another embodiment of the device, shown together with an inhalation valve and variable exhalation valve used therein.
Figure 6B:
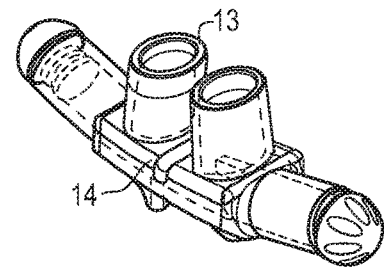
Figure 6C:
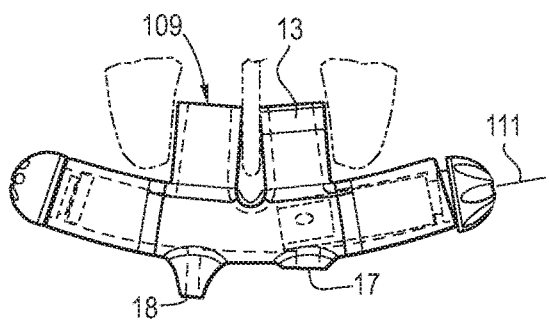
Figure 6D:
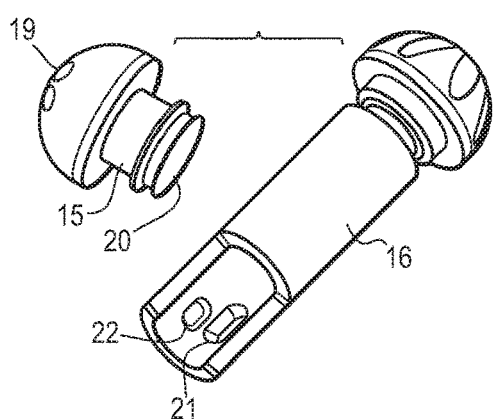

The device disclosed in FIGS. 3A-D is a mouthpiece 5 intended to be inserted in a person's oral cavity, with teeth 101 resting and securing over the bite plate 6 and the tooth cover 7 extending upwardly and downwardly from the bite plate and residing in front of the user's teeth 101. The bite plate 6 includes an interior flange extending upwardly and downwardly from the bite plate in one embodiment, with the flanges and cover define upper and lower channels for the user's teeth. The mouthpiece includes a housing portion extending forwardly from the bite plate and tooth cover. The housing portion, having a generally cylindrical shape, defines a central passageway or opening having a longitudinal axis. Within the mouthpiece 5 central passageway or opening, a valve housing 8 is fitted to accommodate PEP function in the device. The valve housing 8 has a generally cylindrical shape that mates with the central passageway of the mouthpiece housing portion, and may be removably secured or disposed therein. The valve housing has a transverse frame extending across a central passageway of the valve housing. The valve housing 8 hosts an inhalation valve 9, which may be any one of the valves shown in FIGS. 1A-D, secured by a valve post 10 engaging the frame. Within the valve housing 8, positioned for example in the frame, are exhalation ports 11, which may be exposed or covered by a variable resistance dial 12 to achieve various pressure settings on exhalation. The dial 105, configured as an annulus segment in one embodiment, is rotatable mounted to the frame about a longitudinal axis 103 defined by the central passageway. A plurality of longitudinally extending flanges 107 engage the dial 105 and define a track therefore. There may be up to six (6), or more, exhalation ports 11 to accommodate a varying number of settings required for different breathing capabilities. FIGS. 4A and B show the mouthpiece 5 in use, with the inhalation valve 9 open during inhalation (FIG. 4A), and the inhalation valve 9 closed during exhalation, with flow limited to the exhalation ports 11 (FIG. 4B). FIGS. 5A-D show the variable resistance dial 12 in each of four (4) exemplary positions, from a lowest pressure setting (FIG. 5A), wherein the dial leaves uncovered four openings, to a highest pressure setting (FIG. 5D), wherein the dial leave uncovered only one opening. In one embodiment, the number of positions relating to pressure settings is preferably equivalent to the number of exhalation ports 11.

FIGS. 6A-D discloses a device intended to fit and seal inside a person's nostrils 109 via two nostril ports 13. The device includes a mixing chamber 14 coupled to the nostril ports in fluid communication therewith. The mixing chamber has a pair of arms, each having an end port. One port houses an inhalation valve housing 15, while an opposite port houses a variable exhalation resistance dial 16. The mixing chamber 14 also includes an exhalation port 17 and a safety port 18. The exhalation port 17 and safety port 18 are located opposite to the nostril ports 13, but may be exchanged with the ports housing the inhalation valve housing 15 and variable exhalation resistance dial 16. The inhalation valve housing 15 has an end portion, or head, that includes inhalation ports 19, which may consist of one large port or multiple smaller ports. The housing 15 further includes an insert portion, configured as a stem, inserted into the port of the mixing chamber and an inhalation valve 20 coupled to the insert portion. The inhalation valve 20 may be configured as any of the valve types outlined herein with respect to this or other embodiments. The variable exhalation resistance dial 16 includes an end portion, or head, and an insert portion, configured in one embodiment as a cylindrical member having a partial cutout at an end distal to the head. The dial 16 may be rotated about a longitudinal axis 111 to move between a lowest resistance setting, where a first (large) hole 21 is open to (aligned with) the exhalation port 17, a middle resistance setting, where a second (small) hole 22, having a smaller area than the first opening, is open to (aligned with) the exhalation port 17, and a highest resistance setting, where no hole is positioned over or aligned with the exhalation port 17, but rather the annular wall of dial 16 covers the exhalation port, wherein the exhalation path is limited to the safety port 18. It should be understood that additional openings with differential areas may also be provided.

Figure 7A:
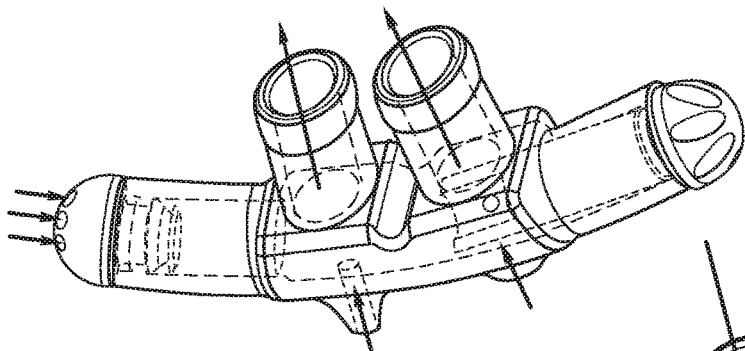
FIGS. 7A and B are isometric views of the device shown in FIG. 6B during inhalation and exhalation respectively.
Figure 7B:
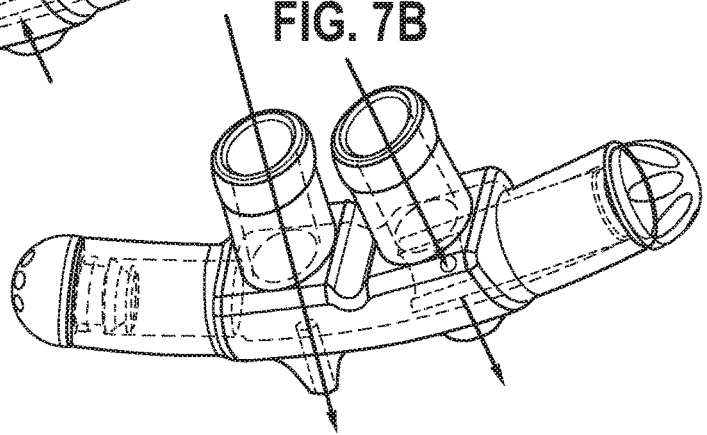
Figure 8A:
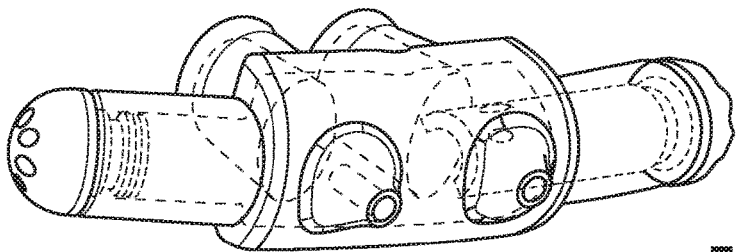
FIGS. 8A-C are bottom isometric views of the device shown in FIG. 6B with the variable exhalation valve shown in different positions ranging from a highest to lowest pressure setting.
Figure 8B:
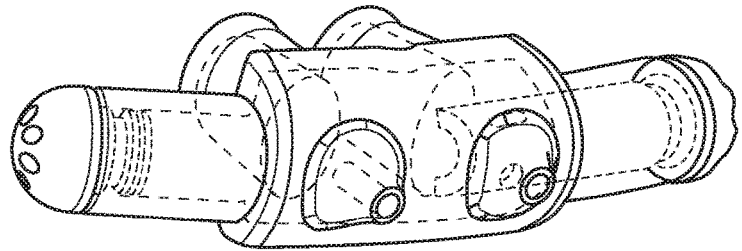
Figure 8C:
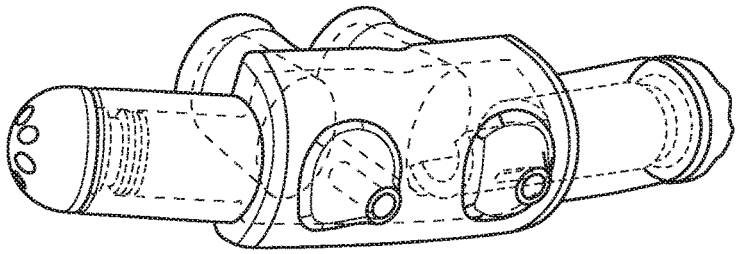

FIGS. 7A and B show the device in use, with air moving primarily through the inhalation ports 19 on inhalation (FIG. 7A) as the valve 20 is opened, and air moving through the exhalation port 17, or safety port 18 on exhalation (FIG. 7B) as the valve 20 is closed. During inhalation (FIG. 7A), air may also move through the exhalation port 17 and safety port 18. The device may be reconfigured to different settings (shown as three (3) in FIGS. 8A-C), achieved by rotating the exhalation resistance dial 16 about a longitudinal axis to move between a high resistance (no hole as shown in FIG. 8A), a small hole/second opening (FIG. 8B) and a large hole/first opening (FIG. 8C). It should be understood that the variable resistance device is not limited to three settings but rather may be configured as a continuously adjustable device, or with some number greater than three, which number may be required to achieve proper functionality for the entire target population.

Figure 9A:
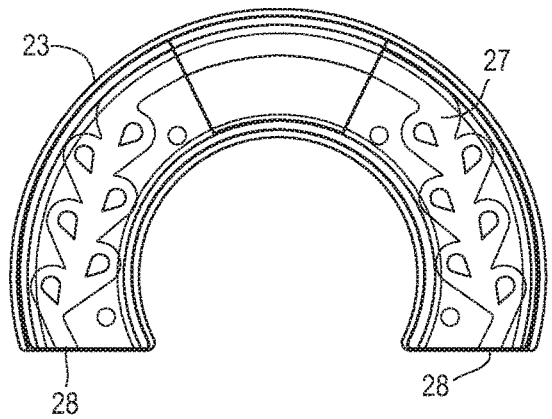
FIGS. 9A-C are a top, exploded isometric and rear view of another embodiment of a device.
Figure 9B:
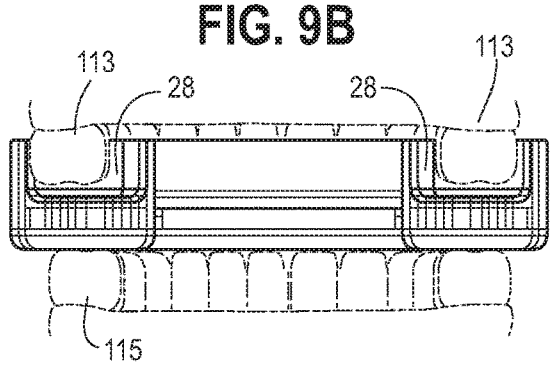
Figure 9C:
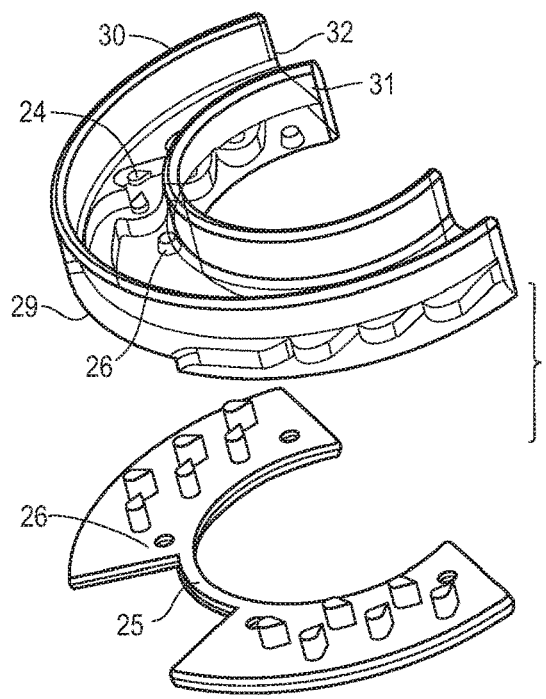
Figure 10A:
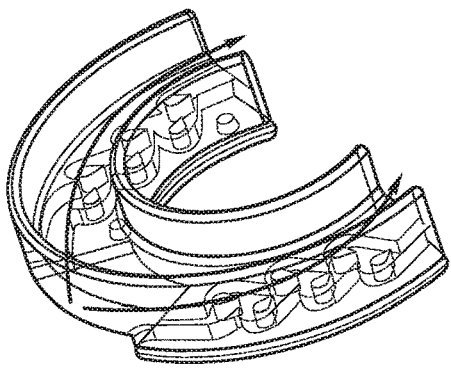
FIGS. 10A and B are isometric view of the device shown in FIG. 9B during inhalation and exhalation respectively.
Figure 10B:
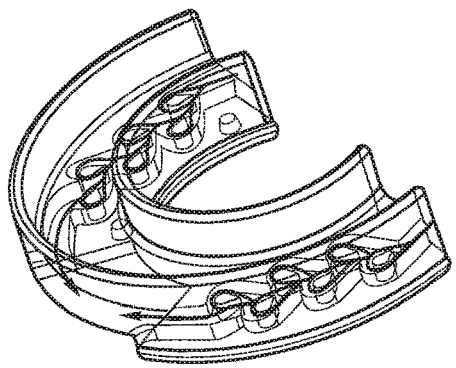
Figure 11A:
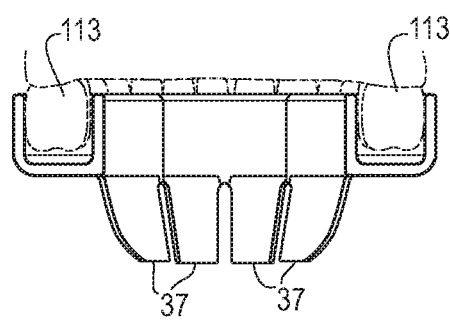
FIGS. 11A-D are rear, isometric, bottom and cross-sectional views of another embodiment of a device.
Figure 11B:
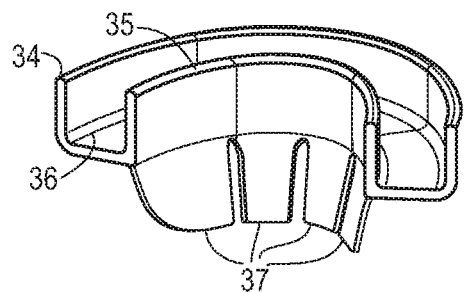
Figure 11C:
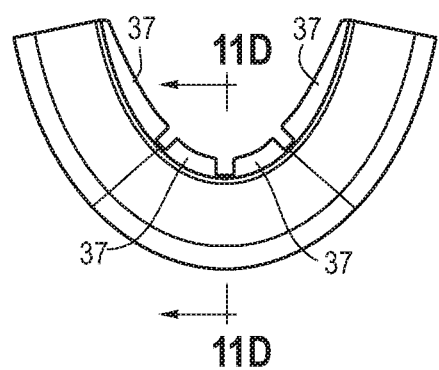
Figure 11D:
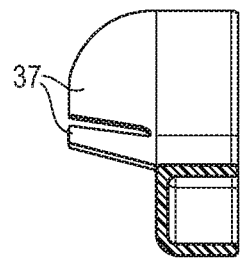

FIGS. 9A-C disclose a mouthpiece 23 intended to be worn in a person's oral cavity to provide PEP. The mouthpiece 23 consists of a flexible upper teeth housing 24 and a rigid or semi-rigid valve geometry case 25, which snap together via a locking mechanism, for example a plurality of posts 26 engaging openings in a snap-fit or interference fit, to create a Tesla valve 27 with no moving parts. The mouthpiece 23 has two breathing channels 28 that join to form a single inhalation/exhalation port 29 in the anterior position of the device. FIGS. 10A and B show the device in use for inhalation and exhalation, respectively, with an understanding that the device is inserted into the user's oral cavity with upper teeth 113 disposed in a channel defined by the housing, and lower teeth 115 engaging a bottom of the case 25. The Tesla valve 27 is designed so that resistance to flow is minimal on inhalation (FIG. 10A) and increased exponentially on exhalation (FIG. 10B). The upper teeth housing 24 has an anterior barrier 30, posterior barrier 31 and bottom bite plate that define the channel, which together form a securing channel 32 where a person's teeth sit 113 and secure the mouthpiece 23 over the upper teeth 113.

Figure 12A:
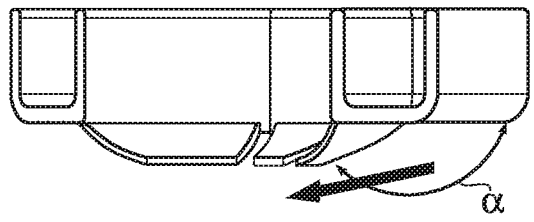
FIGS. 12A and B are isometric side views of the device shown in FIG. 11B during inhalation and exhalation respectively.
Figure 12B:
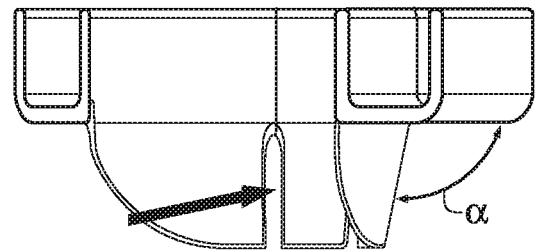

The device in FIGS. 11A-D includes a mouthpiece 33 worn in a person's oral cavity to provide PEP. The mouthpiece 33 has an anterior barrier 34 and a posterior barrier 35, which together with a bite plate form a securing channel 36 that secures the mouthpiece 33 over a person's upper teeth 113. At the back of the mouthpiece 33 and attached to the bottom is a flow blockade 37. FIGS. 12A and B discloses the use of the device during inhalation and exhalation, respectively. The flow blockade 37 moves from a position substantially parallel to the bottom of the mouthpiece 33 during inhalation (FIG. 12A), to a position substantially perpendicular to the bottom of the mouthpiece 33 during exhalation (FIG. 12B), where the flow blockade 37 interferes with a person's teeth and limits exhalation flow. In other words, the flow blockade deforms or deflects during inhalation, for example by bending about end portion coupled to the posterior barrier 35. The flow blockade defines a greater angle α relative to the plane of the bite plate when in the inhalation position as compared with the angle in the exhalation position. The flow blockade 37 may include one large movable barrier, or multiple smaller barriers, for example a plurality of spaced apart fingers (shown in one embodiment as four), that move independently and/or simultaneously with an inhalation flow.

Figure 13A:
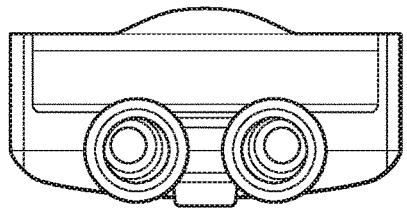
FIGS. 13A-C are front, isometric and bottom views of another embodiment of the device.
Figure 13B:
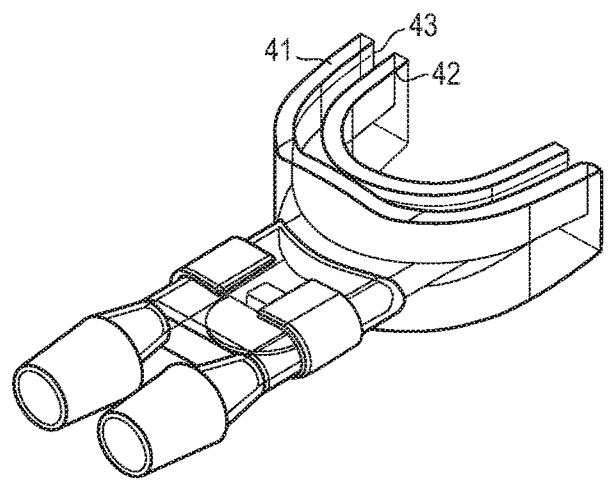
Figure 13C:
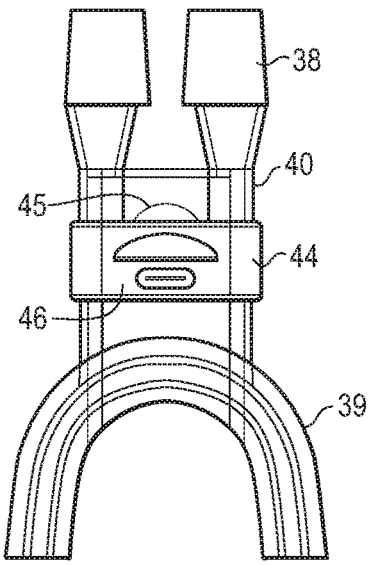
Figure 14A:
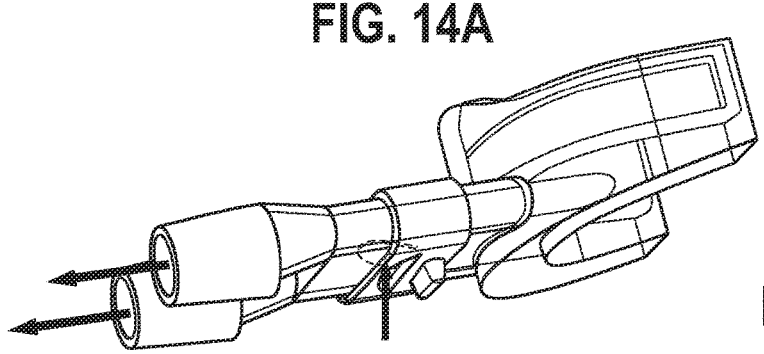
FIGS. 14A-D are isometric views of the device shown in FIG. 13B during nasal and oral inhalation and nasal and oral exhalation respectively.
Figure 14B:
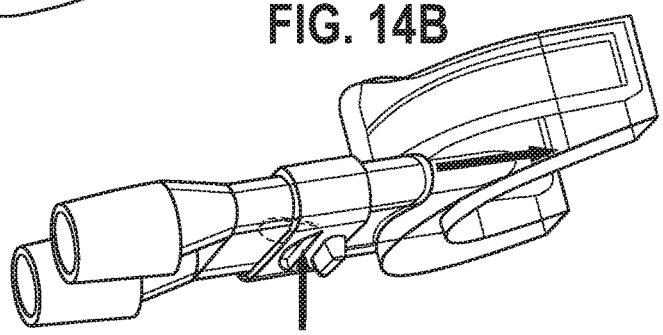
Figure 14C:
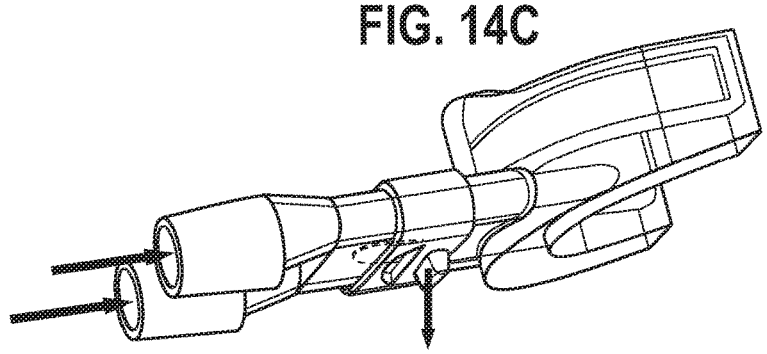
Figure 14D:
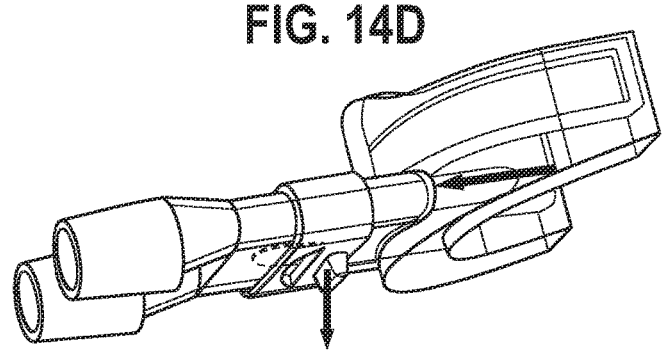
Figure 15A:
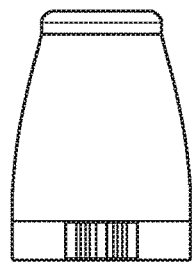
FIGS. 15A-D are top, isometric, rear and side views of another embodiment of the device.
Figure 15B:
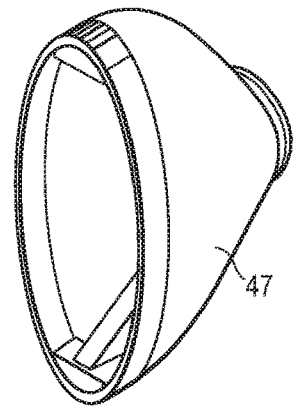
Figure 15C:
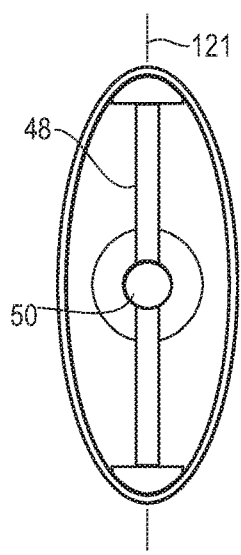
Figure 15D:
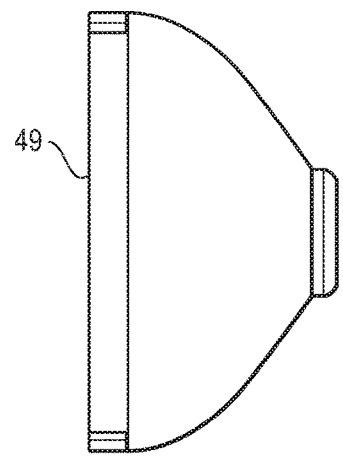

FIGS. 13A-C discloses a device intended to fit into a person's oral and/or nasal cavity to provide PEP regardless of the method of breathing. The nasal plugs 38 secure and seal within a person's nostrils and are connected to a mouthpiece 39 via a flexible connecting chamber 40. The mouthpiece 39 consists of an anterior barrier 41 and posterior barrier 42 that together with a bite plate form a securing channel 43 that secure over a person's teeth 113 to hold the device in place. Coupled to the connecting chamber 40 is a valve housing 44 that secures an inhalation valve 45 (e.g., flap valve) and exhalation valve 46, with the exhalation valve 46 having a much greater resistance than that of the inhalation valve 45. The mechanics of the device are depicted in FIGS. 14A-D, although it should be understood that the connecting chamber 40, which is flexible, may be bent or curved to accommodate the positioning of the nose relative to the mouth. The housing 44 and valves 45, 46 are in fluid communication with both the nasal plugs and mouthpiece, with those components defining flow passageways extending through the nasal plugs and mouthpiece as shown in FIG. 13A.

Figure 16B:
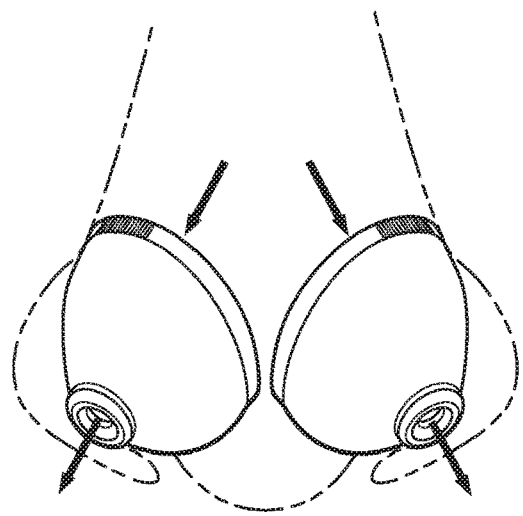
Figure 17A:
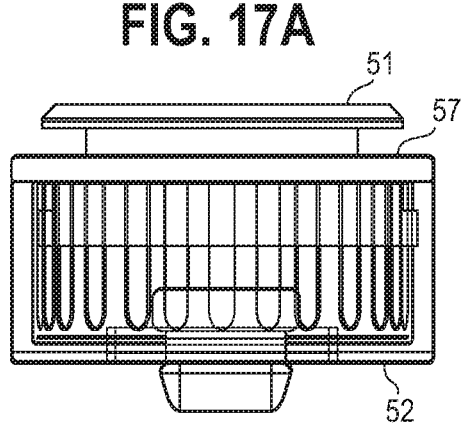
FIGS. 17A-D are top, isometric, front and cross-sectional views of another embodiment of the device.
Figure 17B:
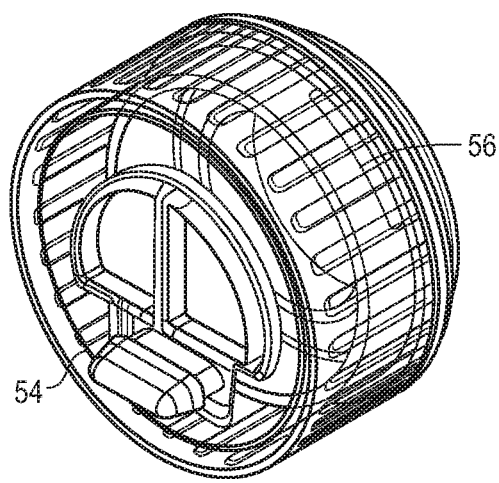
Figure 17C:
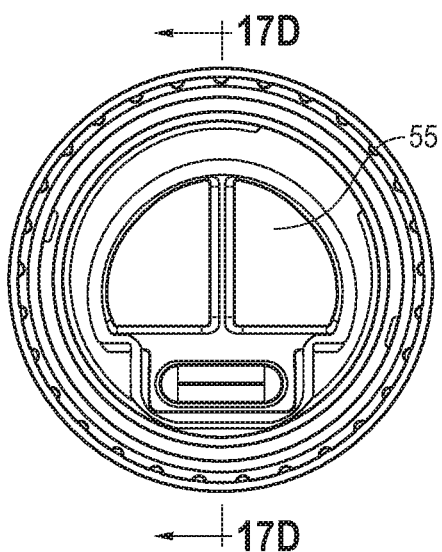
Figure 17D:
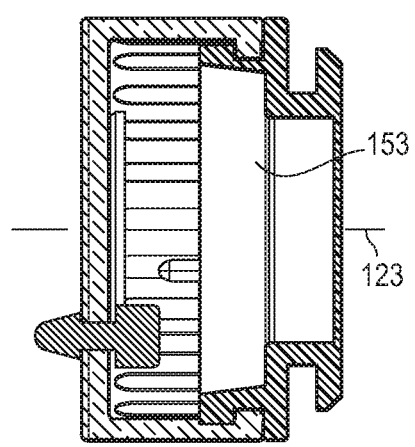
Figure 20A:
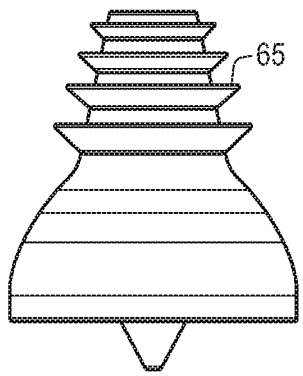
FIGS. 20A-D are top, exploded isometric, front and cross-sectional views of another embodiment of a device.
Figure 20B:
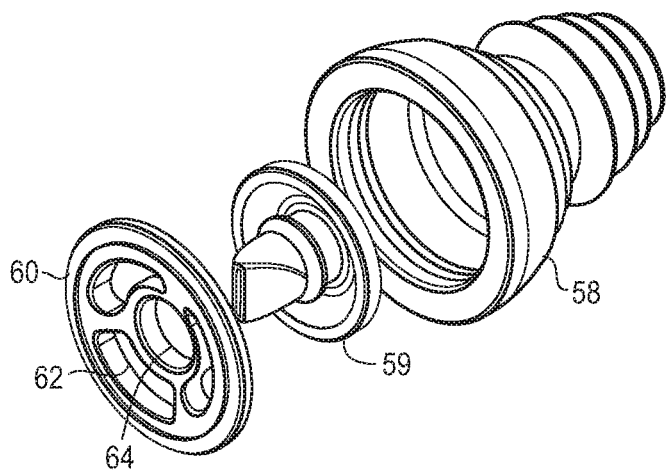
Figure 20C:
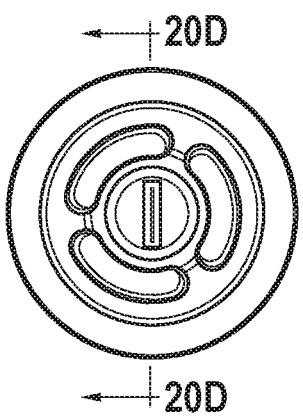
Figure 20D:
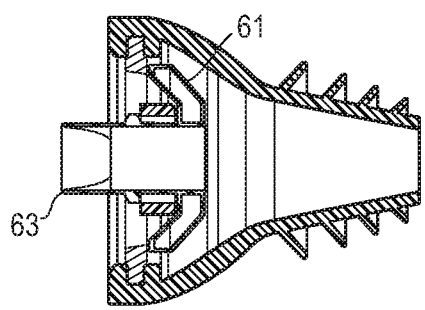

The embodiment in FIGS. 15A-D includes a pair of nasal inserts 47 intended to fit into a person's nostrils. Each of the nasal inserts 47 is made of a flexible material, and has a cup shape, such that it fits comfortably within a person's nose and is able to flex dependent on the air flow. On the inside of the nasal insert 47 are ribs 48 that engage supports engaging an inner surface of the cup shaped inserts are aligned along an axis 121 for added support along the axis while permitting movement or flexing of the cup on both sides of the cup. The device is intended to fit with the large opening 49 furthest in the nostril and the restricted orifice 50 protruding or resting flush with the end of a person's nostril. Intended positioning within the nose is disclosed in FIGS. 16A and B, with inhalation shown in FIG. 16A, and exhalation shown in FIG. 16B. The nasal inserts 47 flex in a concave manner, with the sides of the cup deflecting or deforming inwardly toward the axis, on inhalation, allowing air to travel through the restricted orifice 50 as well as around the sides of the nasal insert 47. Upon exhalation, the nasal inserts 47 flex in a convex manner, with the sides of the cup moving away from the axis to limit flow to the restricted orifice 50.

The embodiment disclosed in FIGS. 17A-D is a device that provides PEP and is intended as an add-on to a nasal mask, nasal pillow, full mask, mouthpiece or any other nasal or oral interface device. The device attaches to an interface device via an adapter 51 to create a complete PEP device. The adapter 51 and resistance dial 52 attach to form a small chamber 53. On the anterior surface of the resistance dial 52 is a valve housing 54 equipped with an inhalation valve 55. The valve may be any variety of valve biased to inhalation flow as disclosed herein with respect to other embodiments. The resistance dial 52 includes a cut out that creates an exhalation port 56 on an outer cylindrical side wall of the dial 52, which aligns with a window 57 on the adapter 51, which has a cylindrical shape with a side wall mating with the side wall of the dial to provide a restricted flow path for exhalation. The flow paths for inhalation and exhalation are shown in FIGS. 18A and B, respectively. As shown in FIGS. 19A-C, the exhalation flow path narrows as the dial 52 and exhalation port 56 are rotated about a central axis 123 on the adapter 51 and misalign with the window 57, thereby closing or reducing the amount of overlapping of the port 56 and window 57.

Figure 21A:
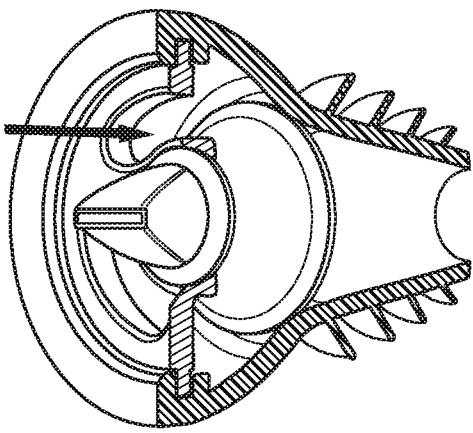
FIGS. 21A and B are partial cross-sectional isometric views of the device shown in FIG. 20B during inhalation and exhalation respectively.
Figure 21B:
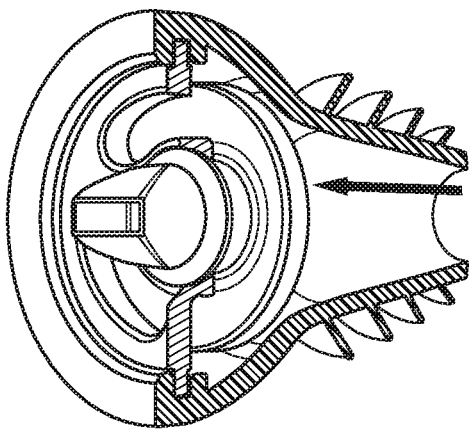
Figure 22A:
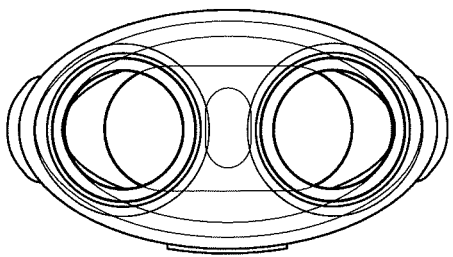
FIGS. 22A-E are top, front, exploded isometric, and bottom views of another embodiment of the device, together with a rotated view of a housing.
Figure 22B:
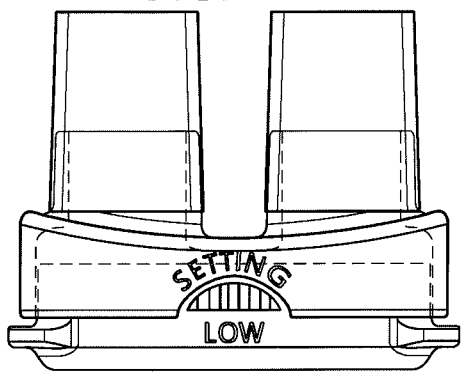
Figure 22C:
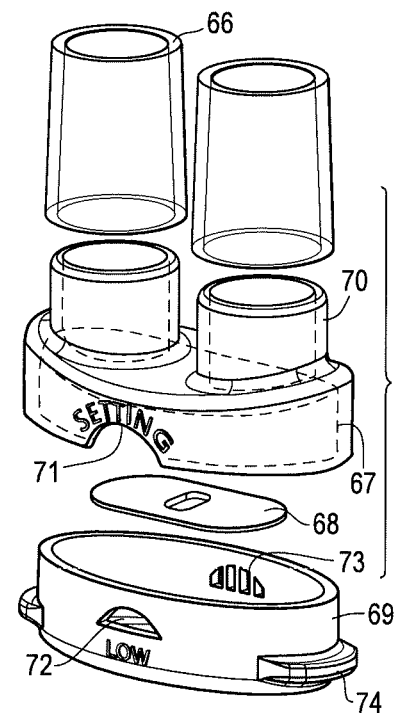
Figure 22D:
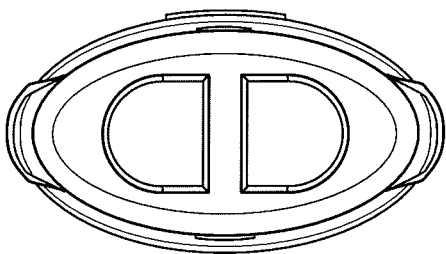
Figure 22E:
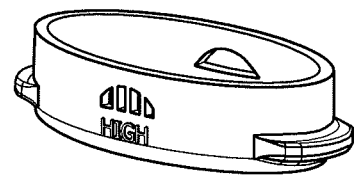

FIGS. 20A-D disclose a nostril insert 58 that is intended to provide PEP for nasal breathing. The device includes three main parts: a nostril insert 58 having a cup shape, a dual valve 59 and a valve housing 60. In other embodiments, these parts may be combined (e.g., integrally formed) or separated further to represent similar function with a different number of components. The dual valve 59 secures within the valve housing 60, such that the inhalation valve 61 rests on a frame having or defining an inhalation window 62 and the exhalation valve 63 rests on or extends through the frame having or defining an exhalation window 64. Single or multiple windows may be present to make up the inhalation window 62 and/or exhalation window 64 elements. The area of the exhalation window(s) 64 is less than that of the inhalation window(s) 62, unless material properties or the nature of the valve types are the main contributing factor to the increased resistance on exhalation. Valve types for both the inhalation valve 61 and exhalation valve 63 may be but are not limited to those disclosed herein with respect to other embodiments. In one embodiment, the valve includes a combined duckbill and umbrella valve, with the duckbill valve closed and the umbrella valve open during inhalation, and the duckbill valve open and the umbrella valve closed during exhalation. To maintain a seal and adequately secure the nostril insert 58 in a person's nostril, valve flanges 65 are located on the end of the nostril insert 58 that protrudes furthest into the nostril. The valve flanges 65 may be made up of one or several flanges. Movement of the dual valve 59 during inhalation and exhalation is shown in FIGS. 21A and B, respectively. In one embodiment (FIGS. 16A and B), the device comprises two nostril inserts 58, one for each nostril. A pair of inserts may be connected with a tether or other connector, or may be integrally molded.

Figure 23A:
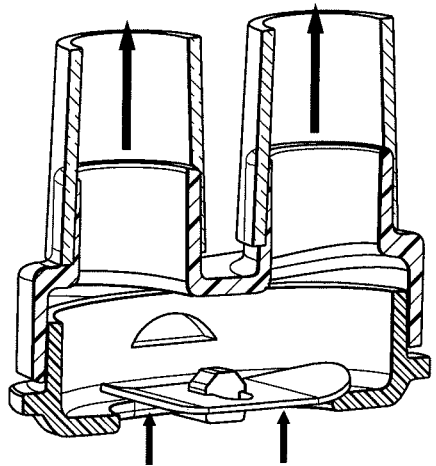
FIGS. 23A and B are cross-sectional isometric views of the device shown in FIG. 22C during inhalation and exhalation respectively.
Figure 23B:
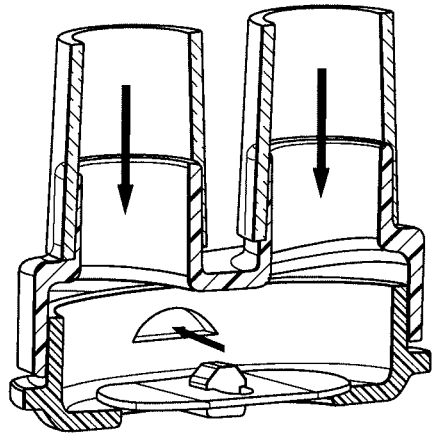
Figure 24A:
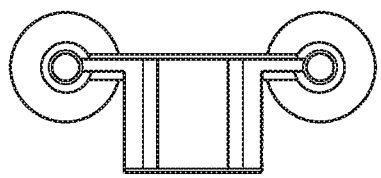
FIGS. 24A-D are front, isometric, top and side views of another embodiment of a device.
Figure 24B:
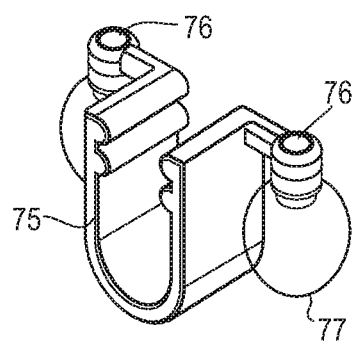
Figure 24C:
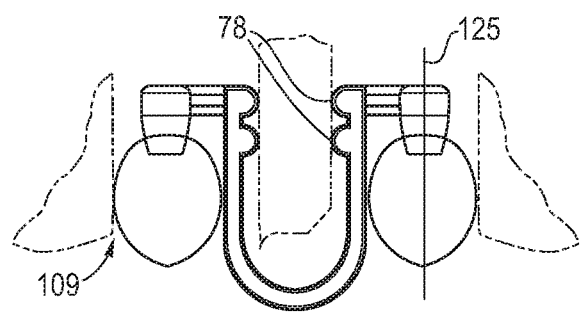
Figure 24D:
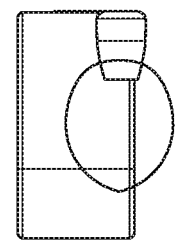

The disclosed device shown in FIGS. 22A-E is inserted in a person's nostrils via the nasal plugs 66 to provide PEP. The device consists of two nasal plugs 66, a nasal setting adapter 67, an inhalation valve 68 and a valve housing 69. The nasal plugs 66, having a generally cylindrical shape, fit over two circular nasal adapters 70, also having a generally cylindrical shape, on the nasal setting adapter 67, which releasably fits with the valve housing 69 by way of a fastening mechanism, for example with a snap fit, interference/press fit, detent, mechanical fastener or combinations thereof. On the bottom of the valve housing 69 is an inhalation valve 68 which may be of any type disclosed herein with respect to other embodiments. The valve is secured to the housing by way of an opening secured over a post. The valve housing 69 may be rotated such that a setting dial 71 may accommodate a low setting exhalation port 72 and a high setting exhalation port 73. The area of the low setting exhalation port 72 is greater than that of the high setting exhalation port 73 to provide less resistance on exhalation, while still maintaining a resistance higher than inhalation. A grip 74 is easily visible on the valve housing 69 to allow for easy manipulation between settings, for example by disengaging the adapter 67 from the housing 69 and rotating one component relative to the other by 180 degrees and reengaging the housing with the adapter. The number of settings may increase or decrease depending on the requirements for the target population and is not limited to the number of settings disclosed in this embodiment. FIGS. 23A and B disclose the intended function of the device during inhalation (FIG. 23A) and exhalation (FIG. 23B).

The disclosed device of FIGS. 24A-D fits securely over the columella portion of a person's nose via a nasal clip 75 having a pair of side walls defining a channel receiving the columella. The clip secures the device to align flow control members extending outwardly from each of the side walls. The flow control members include exhalation ports 76 aligned within each of the nasal passages. The device includes two exhalation ports 76 to interface with both nostrils 109. The exhalation ports 76 may be centered within each nasal passage or slightly skewed from the center, aligned to accommodate the region of maximum flow velocity on exhalation. The flow control member further includes a valve member attached to each exhalation port 76. The valve member is configured as a balloon valve 77 in one embodiment, such that a pair of balloon valves 77 is provided to accommodate both nasal passages. On a posterior side of the device inside the nasal clip 75 are compression ribs 78 that press gently against the nasal septum to secure the device within the nasal passages.

Figure 25A:
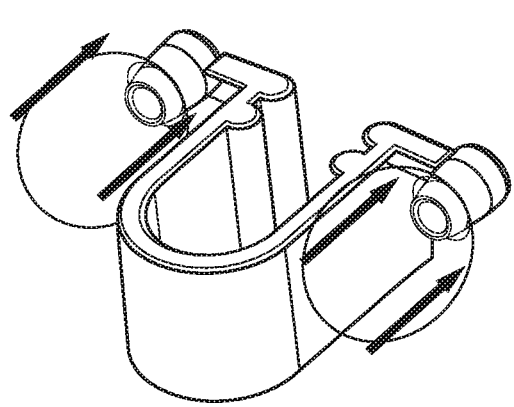
FIGS. 25A and B are isometric views of the device shown in FIG. 24B during inhalation and exhalation.
Figure 25B:
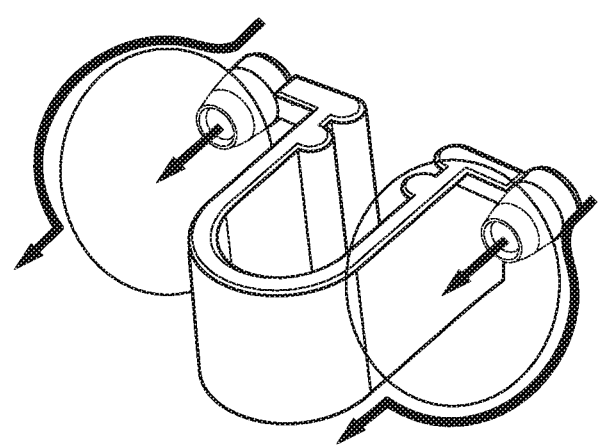
Figure 26A:
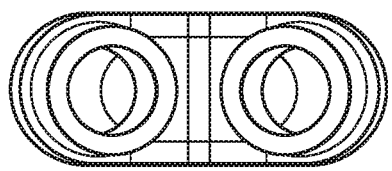
FIGS. 26A-D are top, isometric, front and side views of another embodiment of a device.
Figure 26B:
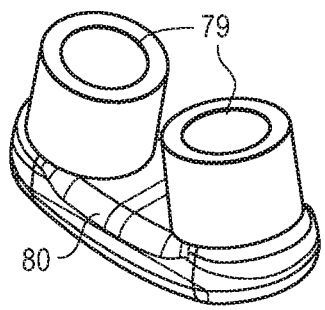
Figure 26C:
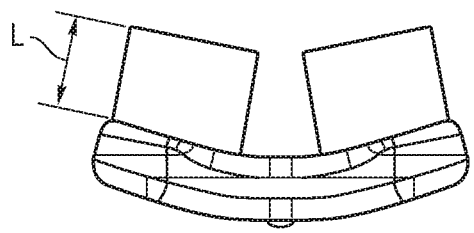
Figure 26D:
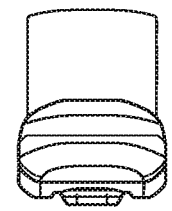

The nasal clip 75 may be made from a material with flexible properties to allow for flexing of the nasal clip 75 during positioning of the device and/or in the resting position within the nasal passages. The flexible material may be a thermoplastic, a flexible rubber/silicone material or metal. Magnetic properties may be incorporated in the compression ribs 78 to further secure the device within the nasal passages, with the magnetic force between the ribs 78 attracting each other through the septum. The balloon valves 77 are designed such that they deflate on inhalation, and define a flow passageway in the nasal passageway having a first cross sectional area perpendicular to a longitudinal axis 125, and inflate on exhalation, and define a second cross sectional area of the flow passageway relative to the axis 124, as shown in FIGS. 25A and B, with the first cross-sectional area being greater than the second cross-sectional area. Stated another way, the cross-sectional area of the balloon valve is greater during exhalation, thereby decreasing the cross-sectional area of the flow passageway. The walls of the balloon valve 77 are thin (e.g., less than 1 mm in thickness), and the exhalation ports 76 are large enough (e.g., greater than 2 mm diameter) to allow the balloon valves 77 to inflate completely within the first 500 ms of exhalation. Once inflated, the balloon valves 77 block flow through the exhalation path, providing positive exhalation pressure in the airways. Upon inhalation, the balloon valves 77 deflate completely within the first 500 ms of inhalation, creating a cross-sectional and surface area within the nasal passage for air to flow with minimal resistance, e.g., less than 2.4 cmH$_2$O/L/S, created by the device. In one embodiment, the balloon valves 77 may be incorporated into a different nasal device, such as the embodiment of FIGS. 1A-D or FIGS. 20A-D, and operated in the same way.

Referring to the embodiment shown in FIGS. 26A-D, the device provides positive expiratory pressure through the nasal passages. The device secures within the nasal passageways via porous nasal inserts 79, having a cylindrical shape defining a central passageway, with the inserts having a predetermined length L, e.g., 10 mm. For example, the inserts may be made of foam, a polymer compound, polyethylene, bamboo, tencel, wool, cotton, nylon, and/or a metal based material, or combinations thereof. The pair of nasal inserts 79 are connected to a body 80 that rests against or is in close proximity to the outside of the nasal passages. The body 80 may be made of a flexible material, such that the positions of the nasal inserts 79 may be altered, for example by manipulating the body, so as to accommodate the anatomy of the particular user's nostrils. On the anterior end of the body 80 is an inhalation channel 81, created by an opening with a valve post 82 in the center. A one-way inhalation valve 83 is secured to the valve post 82 and rests against the inside of the inhalation channel, which defines a valve seat, in the closed position. The valve 83 may control flow to both inserts, for example by way of opposite flaps.

Figure 27A:
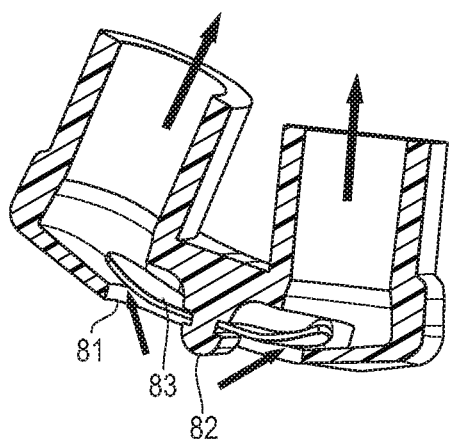
FIGS. 27A and B are cross-sectional views of the device shown in FIG. 26B during inhalation and exhalation respectively.
Figure 27B:
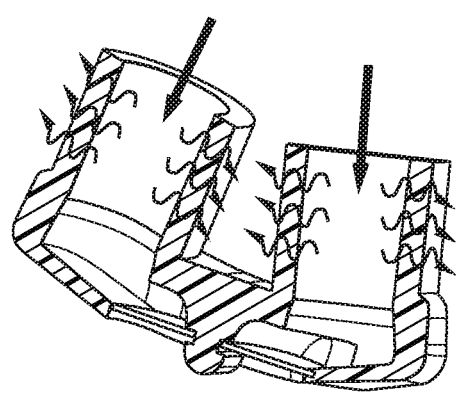

FIGS. 27A and B disclose the operation of the device, with the inhalation valve 83 open on inhalation and closed on exhalation. During exhalation, air flows or travels through the pores of the porous nasal inserts 79, providing an increased resistance and resulting a positive airway pressure. The level of resistance achieved is dependent on the material selection of the porous nasal inserts 79 as well as the compression required to create a seal within the nostrils, and various geometries and pore sizes may be chosen to allow for selection of the optimal resistance for each individual. The porous inserts 79 are flexible to accommodate compression and to allow the inserts to seal within each nasal passage. In one embodiment, the porous nasal inserts 79 may be removably attached to the body 80 to allow the user to customize the device and interchange inserts 79 providing various resistance levels to achieve a desired positive airway pressure on exhalation. The porous nasal inserts 79 also have the added benefit of trapping moisture in the user's breath on exhalation, increasing the humidity of inhaled air and improving hydration levels.

Figure 28A:
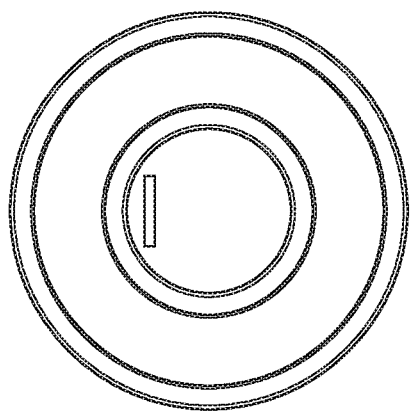
FIGS. 28A-C are top, side and bottom views of another embodiment of a device.
Figure 28B:
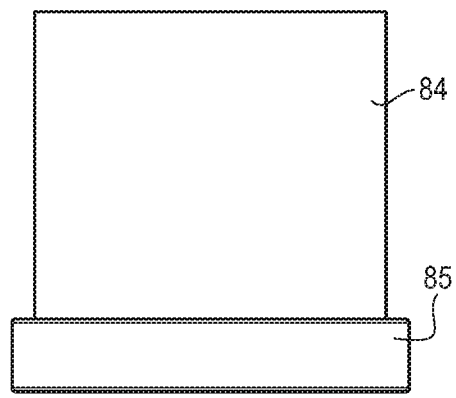
Figure 28C:
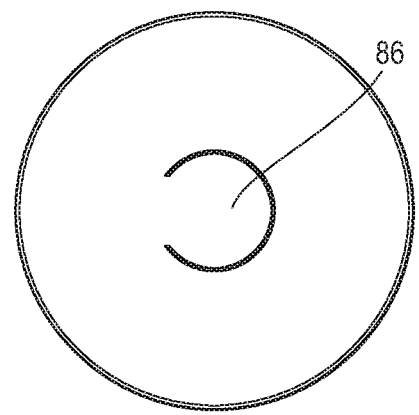
Figure 29A:
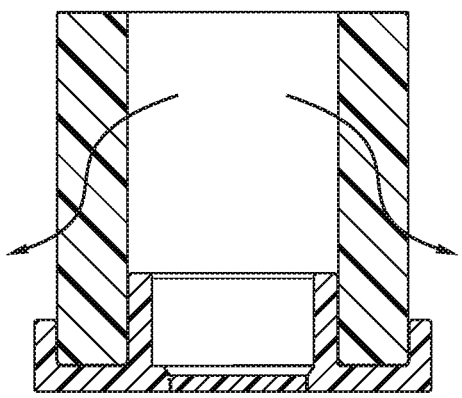
FIGS. 29A and B are cross-sectional views of the device shown in FIG. 28B during inhalation and exhalation respectively.
Figure 29B:
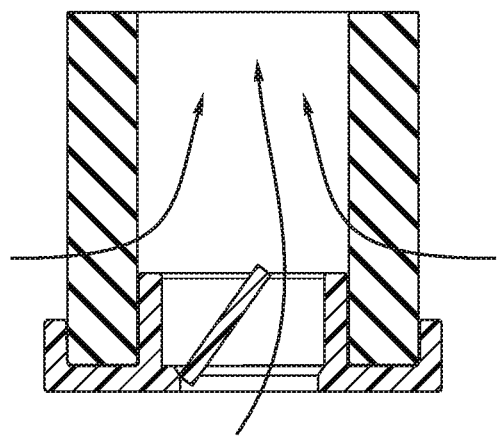

FIGS. 28A-C disclose a nasal device that may be inserted and secured to the inside of the user's nostril. A tube portion 84, having a cylindrical shape, includes an open-cell, flexible foam configured to provide a resistance to flow that produces a sufficient PEP during a passive or active exhalation. A distal end of the foam contains a rigid cap 85 that may be integrally formed with the tube portion as a one-piece unit, or coupled thereto as a separate part. The cap may have a greater diameter than a diameter of the tube portion, thereby forming a shoulder along an end of the cap. The cap has an annular channel that receives a cylindrical end portion of the tube portion as shown in FIGS. 29A and B. The cap 85 has a one-way valve 86, which is located concentric to the foam tube and is configured to allow inspiratory flow while closing completely during exhalation. The valve 86 may be formed as a flap valve by way of a C-shaped slit being formed in the cap, with a bridge portion providing a hinge for the valve. The cap forms a valve seat, which may be tapered as shown in FIG. 29A. The tube structure 84 is configured such that most of the inspiratory flow passes through the center with low resistance and a small faction passes through the foam for heat and moisture exchange. In addition to humidifying the inspired air, the foam absorbs condensation or secretions to improve user comfort. The tube formation also prevents over compression of the foam structure which improves the consistency of the foam's resistance to flow. As shown in FIG. 29B, during inspiration, the valve 86 opens into the interior of the cap 85 and allows flow through the central passageway of the tube portion. During exhalation, as shown in FIG. 29A, the valve closes, with air flow through the foam tube portion, and optionally through a leak passage formed by the valve interface with the cap or through an orifice in the center of the valve.

In another embodiment, a foam nasal insert is configured to be inserted and secured on the inside of the user's nostril. The foam is manufactured such that its resistance to flow during inhalation is significantly (20× to 30×) lower than the exhalation resistance.

Figure 30A:
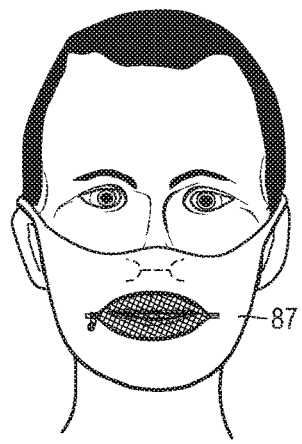
FIGS. 30A and B are front views of another embodiment of a device applied to a user in a non-PEP and PEP configuration respectively.
Figure 30B:
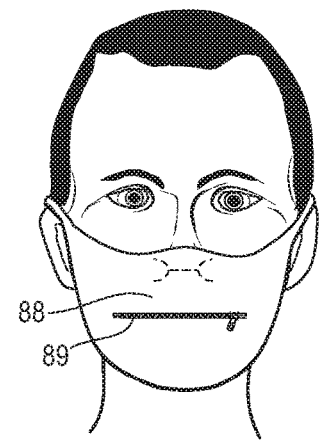

Referring to FIGS. 30A and B, a mask 87, which may be configured as, or incorporated into and including, a balaclava, neck gaiter, neck warmer, scarf, buff or other device secured to the user and covering the mouth and nostrils. The mask 87 has a removable region 88 of increased resistance to flow on exhalation that supplies the user with PEP therapy. Inspiratory resistance of the removable region 88 is very low. The region 88 may be removed, for example by creating an opening, via a fastener 89, for example and without limitation buttons, hook/loop fasteners (e.g., VEL-CRO fasteners) laces, zippers, reclosable fasteners (e.g., slider) to allow for unobstructed breathing when PEP is not desired. In this way, it should be understood that the phrase removable region refers to a portion of the mask that may be removed from covering the user's face, whether by making an opening, which does not remove any actual material or component, or by removing a portion of the mask. Since humidity at higher altitudes is low, the fabric of the mask 87 may also serve as a heat and moisture exchanger to help humidify the inspired air. An optional inhalation region may be incorporated into the mask adjacent the nostrils of the user. For example, the inhalation region may include inhalation valves (e.g., flaps) incorporated into the mask, which valves allow greater inspiratory flow.

Figure 31A:
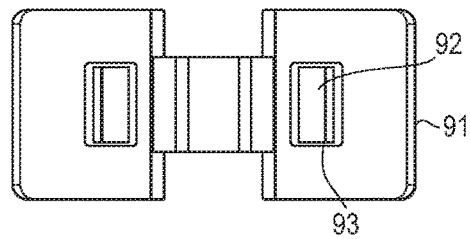
FIGS. 31A-C are top, front and side views of another embodiment of a device.
Figure 31B:
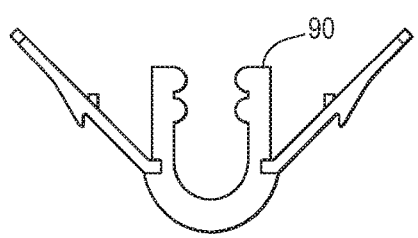
Figure 31C:
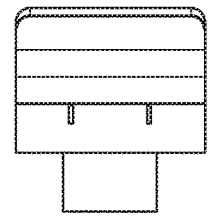
Figure 32A:
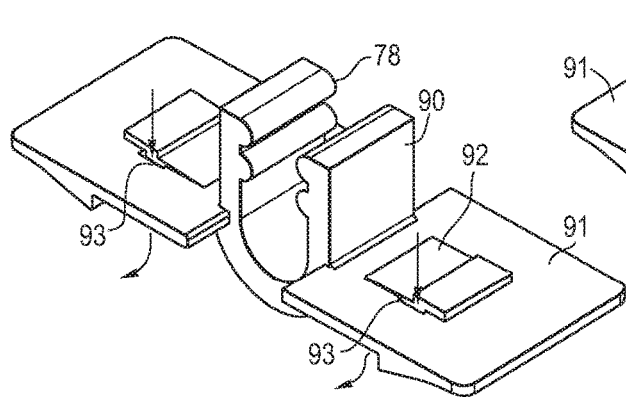
FIGS. 32A and B are isometric views of the device shown in FIGS. 31A-C during exhalation and inhalation respectively.
Figure 32B:
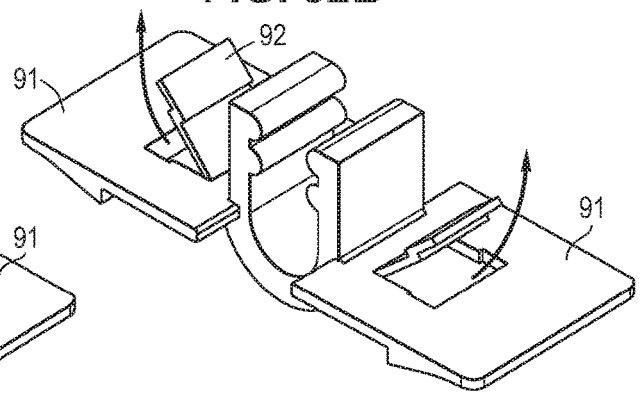

Referring to FIGS. 31A-C, a nasal device is fastened to the user by engaging the columella (lower part of the nasal septum) of the nose with a clip 90, which may be configured with ribs 78 that help grip the nasal tissue. A flap 91 extends outwardly from both sides of the clip 90. A distal freed end of each flap 91 seals with an outer perimeter of the nostrils when the device is in use, or engaged with the columella. A one-way inhalation valve 92 is situated on each flap 91 such that inspiratory flow may pass through with minimal obstruction and exhalation flow is forced through small openings 93 on either side of the valve 92 to provide PEP. The valve is formed as a flap valve having an end portion with a free edge and an opposite end pivotally coupled to the flap 91. The end portion has a greater geometry than the opening in the flap, such that the flap valve seats against a surface of the flap when closed. The flaps 91 have enough resistance to bending or pivoting such that when in use, the expiratory pressure is not sufficient to lift the flaps off the perimeter/periphery of the nostril. FIG. 32B shows the valves 92 opening during inspiration, while FIG. 32A shows the air flow through the openings during exhalation. The flaps have an extension to the valve landing on a side thereof opposite the valve to increase the sealing area of the valve and prevent the valve from blowing through during exhalation. The flaps 91 may be integrally formed with the clip, or separately formed and coupled thereto as shown in FIG. 31B. The flaps may be pivotally coupled to the clip, but are biased toward the clip so as to maintain a good seal with the end of the nose, or perimeter of the nostril. As shown in FIGS. 32A and B, the flaps may have a greater width than the clip.

The small openings 94 may be closed, with the flaps 91 lifting off the surface of the end of the nostril to provide an expiratory flow path. In such an embodiment, then pressure falls below a threshold, the flaps 91 will seal back against the end of the nostrils and prevent further expiratory flow. In this embodiment, the device behaves as a threshold-based PEP device rather than a restrictive orifice type device.

Figure 33A:
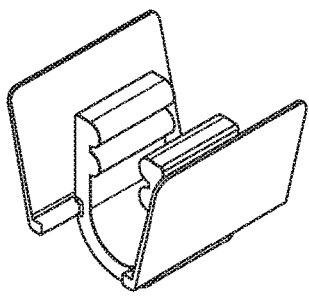
FIGS. 33A-C are isometric, front and side views of another embodiment of a device.
Figure 33B:
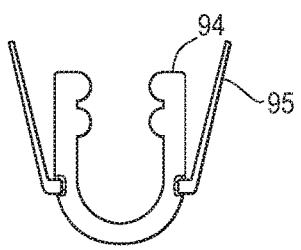
Figure 33C:
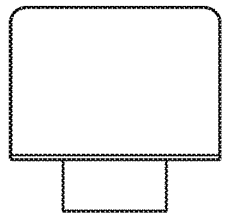

FIGS. 33A-C show a nasal device that is secured to the columella of the user with a clip 90. A flap 95 extends outwardly from both sides of the clip 90. Each flap 95 extends into the nostril and seals against the nasal tissue, providing PEP. The flaps are pivotally, or hingedly coupled to the clip, for example with an integrally formed living hinge, or by way of a hinge pin (separate or integrally formed with the flap and engaging a socket in the clip).

Figure 34A:
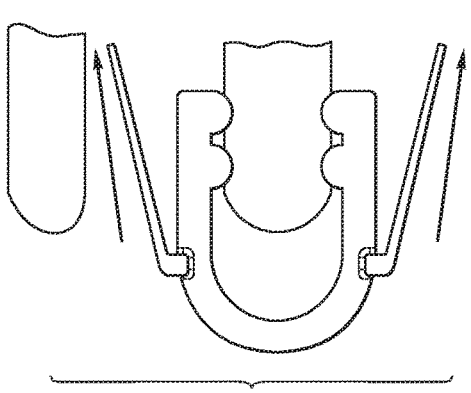
FIGS. 34A and B are front views of the device shown in FIGS. 33A-C during inhalation and exhalation respectively.
Figure 34B:
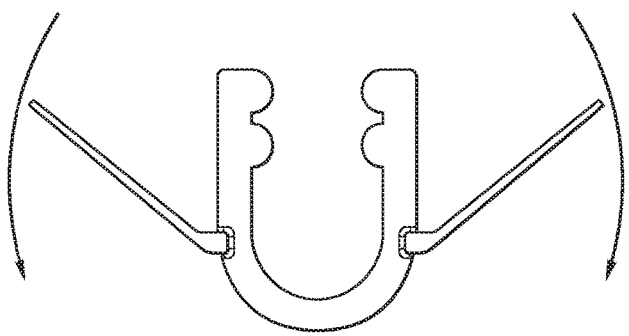

FIG. 34A shows the flap 95, functioning as an inhalation valve, opening during inspiration by pivoting about a pivot axis, or bending about a virtual axis. The inspiratory pressure and resilient of the flaps 95 allow the flaps 95 to be drawn back towards the clip 94, allowing for a nearly unobstructed inspiratory flow path. The flaps 95 may have a small orifice depending on the effectiveness of the seal on the internal nostril wall. FIG. 34B shows the air flow through the openings during exhalation, wherein the flaps 95 engage the nasal tissue and block the flow creating PEP.

Figure 35A:
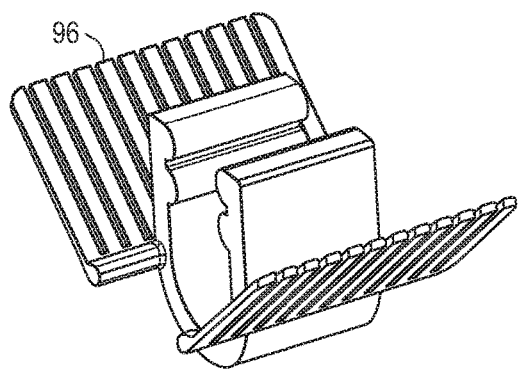
FIGS. 35A and B are isometric views of other embodiments of the device shown in FIGS. 33A-C.

Referring to FIGS. 35 A and B, the flaps may be customized to accommodate a wide variety of nasal shapes and sizes. For example, as shown in FIG. 35A, each flap 95 may be configured as an array or series of a plurality of spaced apart fingers 96. One or more of the fingers may be removed, for example by tearing or cutting, so to alter the fit within the nostril and/or alter the amount of PEP. The fingers may be provided with lines of weakness to facilitate the removal, for example perforations.

Figure 35B:
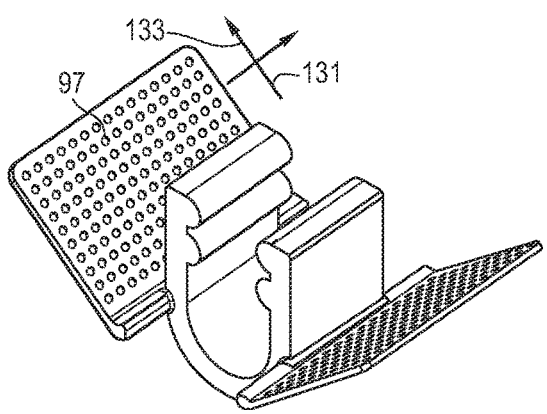
Figure 36A:
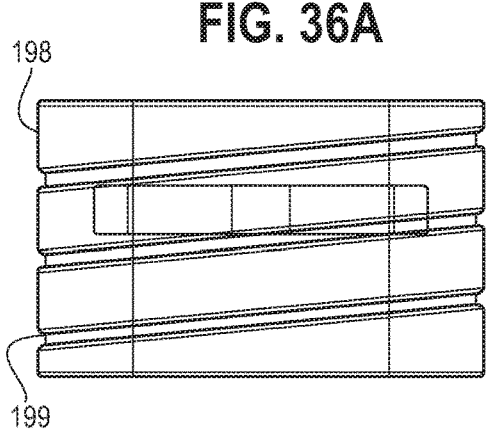
FIGS. 36A-D are top, isometric, front and side views of another embodiment of a device.
Figure 36B:
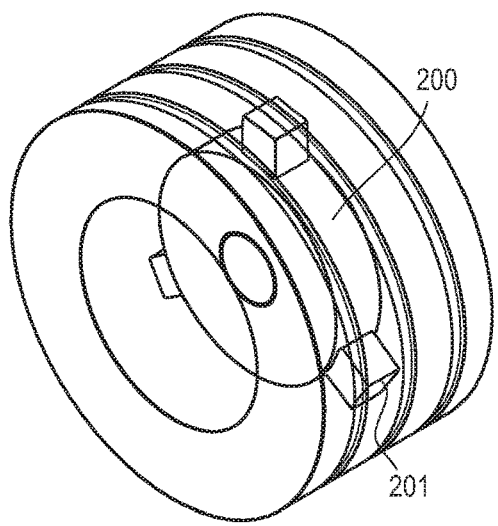
Figure 36C:
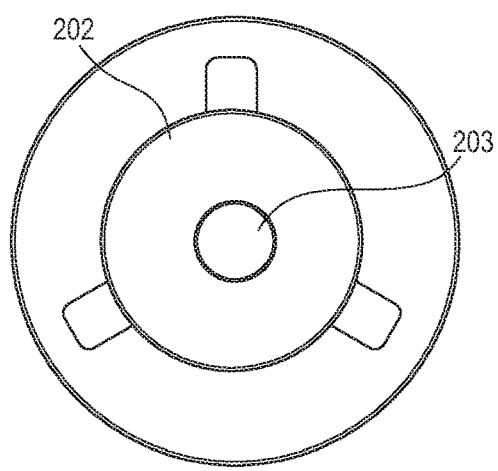
Figure 36D:
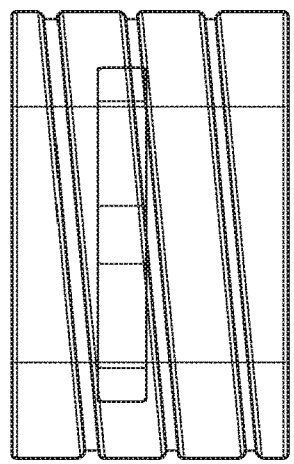

Referring to FIG. 35B, each flap may be provided with an array or grid of perforations in both a longitudinal and lateral direction, allowing the user to separate (e.g., tear or cut) the flap along either axis 131, 133 and shorten the flap and/or fingers, individually or collectively, to form a plurality of flap components, for example by creating a plurality of fingers that may have different widths and/or lengths, and/or create greater or lesser spaces between fingers, etc.

Referring to FIGS. 36A-D, a nasal device, or nasal insert, is configured to be inserted in a nasal passage to provide increased resistance during exhalation. The device includes a tubular body 198, formed as a cylindrical housing having a central passageway. The body has a thread 199 extending around a periphery of the body. The thread 199 is interiorly formed, meaning it is formed as a groove extending radially inwardly from an exterior surface of the body. In other embodiments, the thread may be exteriorly formed, wherein the thread extends radially outwardly from the exterior surface of the body. In either embodiment, the thread formed on the outer surface engages the nasal tissue of the user and secures the device in the user's nasal passageway by turning or rotating the device as it is inserted into the nasal passage.

A valve seat 200, formed as an annular ring shaped member defining a opening, extends transversely across the central passageway of the body. A plurality of circumferentially spaced locking tabs secure the valve seat 200 to the body. The tabs may be formed on the valve seat and are inserted into openings in an interior surface of the body defining the central passageway, or the tabs may be formed on the body and engage the valve seat, for example by being disposed in openings in the side of the valve seat, e.g., with a snap fit. The valve seat 200 has a sealing surface facing downstream in a longitudinal direction for mating with a valve 202. The valve 202 has an edge portion secured to the body or valve seat, permitting the valve 202 to pivot or rotate away from the valve seat during inhalation as shown in FIG.

37A. It should be understood that other types of connections and valves may also be suitable.

Figure 37A:
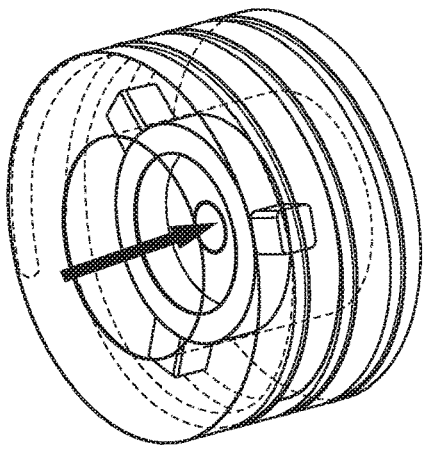
FIGS. 37A and B are isometric views of the device shown in FIG. 36B during inhalation and exhalation respectively.

The valve 202 has an annular shape, with a central opening or orifice 203. During inhalation, as shown in FIG. 37A, the valve 202 moves away from an at rest position, wherein the valve is seated against the sealing surface of the valve, to an open position, to an inhalation position wherein the valve is moved (e.g. pivoted or translated) off of the valve seat so as to allow air flow through the opening defined by the valve seat.

Figure 37B:
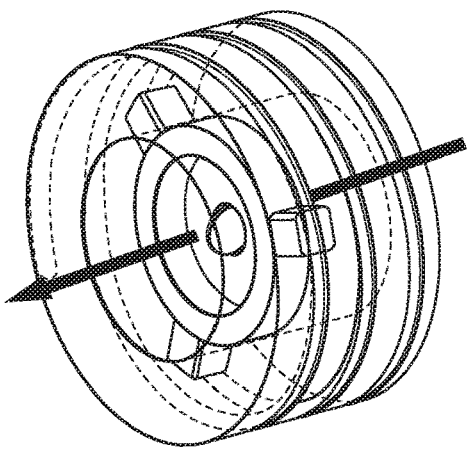
Figure 38A:
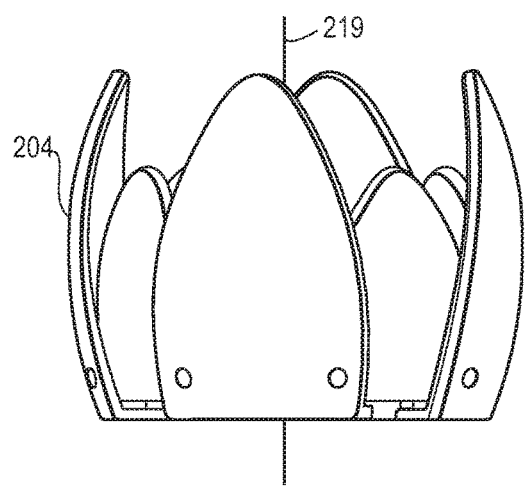
FIGS. 38A-D are top, isometric, front and side views of another embodiment of a device.
Figure 38B:
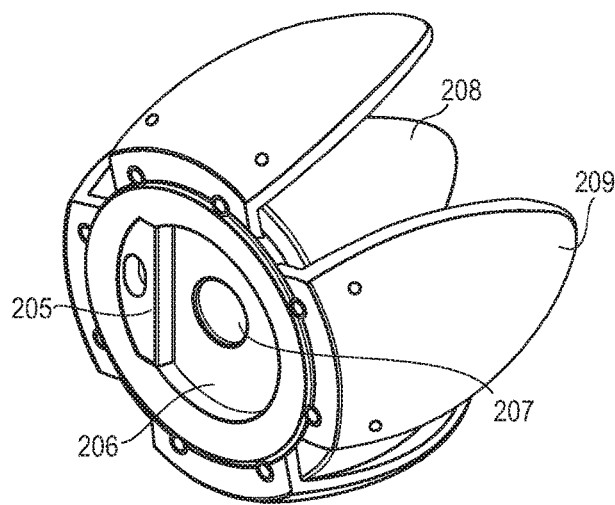
Figure 38C:
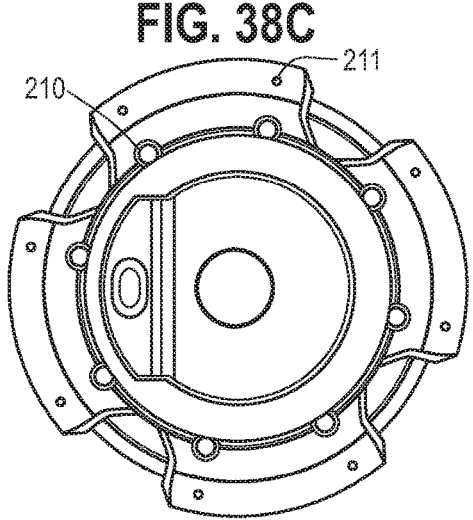
Figure 38D:
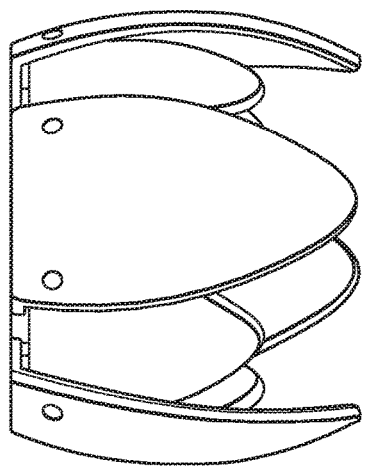
Figure 39A:
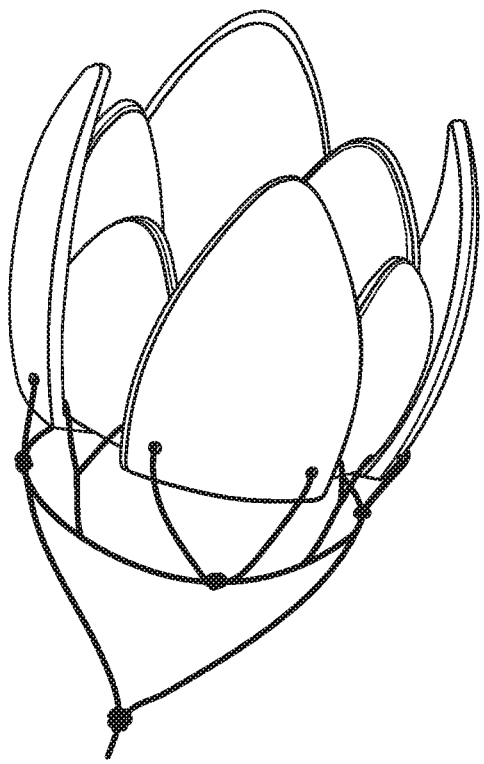
FIGS. 39A and B are isometric views of the device shown in FIG. 38B during inhalation and exhalation respectively.
Figure 39B:
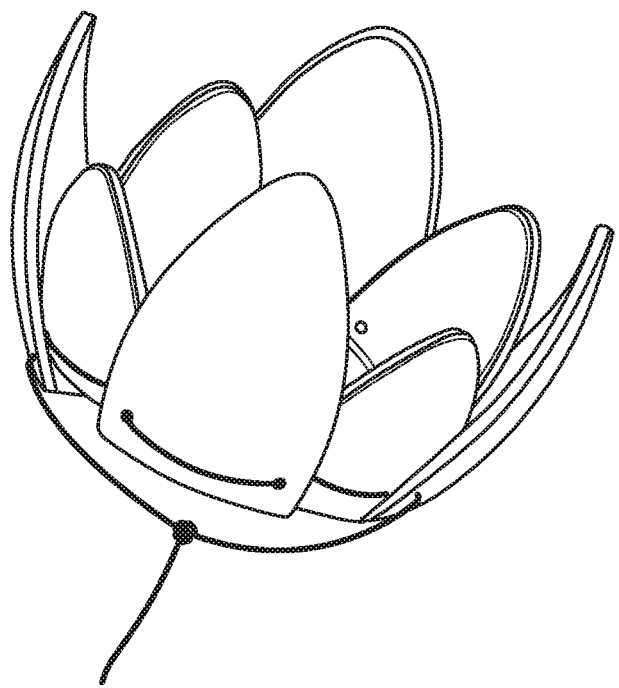

During exhalation, as shown in FIG. 37B, the valve 202 moves from the inhalation to the at-rest position (also defining an exhalation position), wherein the valve 202 seals against the sealing surface of the valve seat. Exhalation air flow is there by limited to flow through the orifice 203. Different valves, with different sized orifices (varied area of the opening), may be removable installed in, or coupled to, the body to provide varied or different resistances to accommodate different individuals and/or environments/activities (e.g., different elevations and/or rest v. active use). The body may be made of a rigid or flexible material, and may formed of a porous material (e.g., foam), or include a layer (e.g., cylindrical) of porous material, to aid in filtering air and act as a heat and moisture exchange (HME) to humidify the inhaled air. A tool may be provided to help insert and remove the device from the nasal passage, as the device is intended in one embodiment to be inserted completely into the nasal passage of the nose. In some embodiments, it is understood that the tool may be an item commonly in the possession of a user, for example a key, whistle, eyeglass temple, etc.

It should be understood that a pair of devices may be used, with each body 198 inserted into a respective nasal passageway.

Referring to FIGS. 38A-D, a nasal insert 204 is configured to be inserted in a nasal passage to provide increased resistance during exhalation. The nasal insert 204 has a housing 205, or base, extending perpendicular to a longitudinal axis 219 of the nasal passageway. A valve 206, configured similar to the valve 202, with an annular ring-like shape and having a central orifice 207, is moveable secured to the base, for example by way of a hinge defined by a post. The base has a ring-like shape with a central opening, and defines a valve seat having a sealing surface formed on a downstream surface of the base. The valve opens, or moves off the sealing surface during inhalation as disclosed previously, and seats against the sealing surface during exhalation, with flow thereby being limited to flow through the orifice 207. Different valves with differently sized orifices may be removably coupled to the base to accommodate different users, environments and levels of activity (at-rest v. active). To anchor the device to the nasal passageway, a plurality of anchor members, configured in one embodiment as petal shaped members, have a first end pivotally coupled to the base and an opposite free end, terminating in a curved point, which engages the nasal tissue of the user. The anchors may be arranged with a plurality of circumferentially spaced first petal shaped members 209, and a plurality of circumferentially spaced second petal shaped members 208, with the second petal shaped members offset with, and positioned in the gaps between, the first petal shaped members. In one embodiment, the first petal shaped members are longer, or extend a greater distance in a longitudinal direction 219, than the second petal shaped members. In one embodiment, the second petal shaped members are disposed radially interiorly of the first petal shaped members, with the sides of the adjacent members overlapping. The first and second petal shaped members may be hingedly, or pivotally coupled to the base. The petal shaped members may each have a base flange at the first end that overlaps with the base member. The first and second petal shaped members may be integrally formed with the base, e.g., with a living hinge providing the relative pivotal movement between the base and petal shaped members, or with a separate hinge pin. Or the base flanges may be secured to the base, with a living hinge formed between the petal shaped member and the base flanges. The first and second petal shaped members rotate, or pivot, radially away from and toward the axis 219 during operation, or insertion.

The first and second petal shaped members, or anchor members, are preferably rigid bodies. To actuate, or pivot, the petal shaped members, an actuation member, for example a wire or thread, or network/web thereof, extends through adjacent openings 210, 211 formed in the base and petal shaped members, with the overlapping portions of the first and second petal shaped portions having aligned openings 211. The various wires/threads connected to each of the petal shaped members, which are secondary members, are centrally connected as, or connected to, a central or primary cord/pull. The actuation member, and in particular the central pull member, may be pulled by the user from outside the nasal passageway to open and engage the petal shaped members 208, 209 with the nasal tissue of the user and thereby provide an adjustable fit to accommodate different users. In one embodiment, the orifice 207 may be omitted, with small air passageways being formed between adjacent and overlapping petal shaped members 208, 209 to restrict the flow during exhalation and increase the oxygen saturation levels.

Figure 40A:
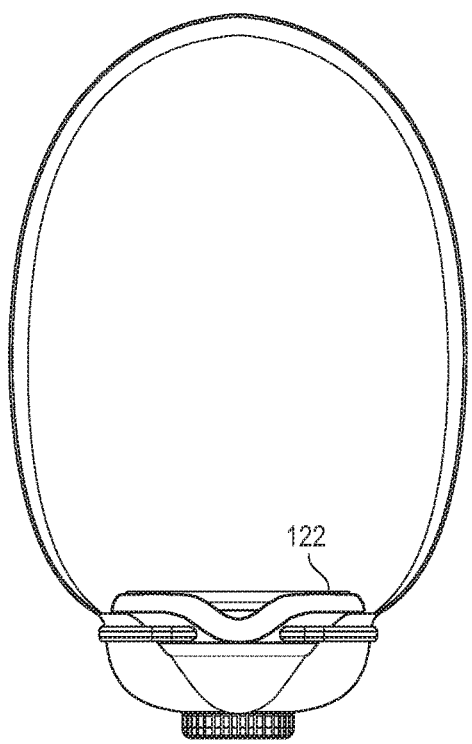
FIGS. 40A-D are top, section, front and side views of another embodiment of a device.
Figure 40B:
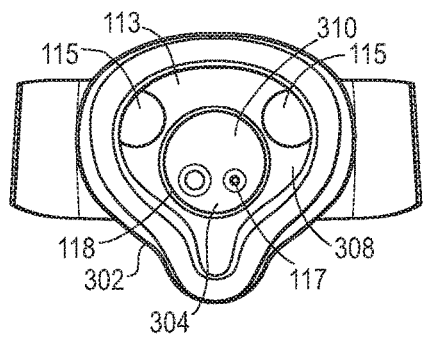
Figure 40C:
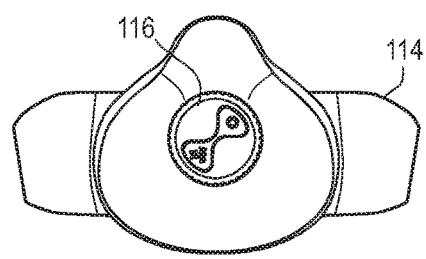
Figure 40D:
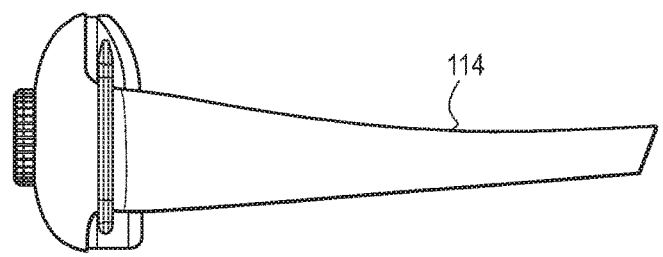
Figure 41A:
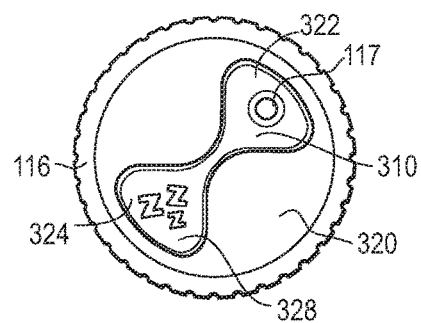
FIGS. 41A and B are front views of a dial.
Figure 41B:
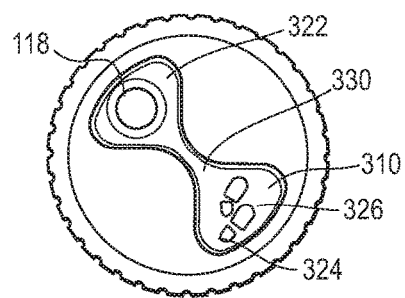
Figure 42A:
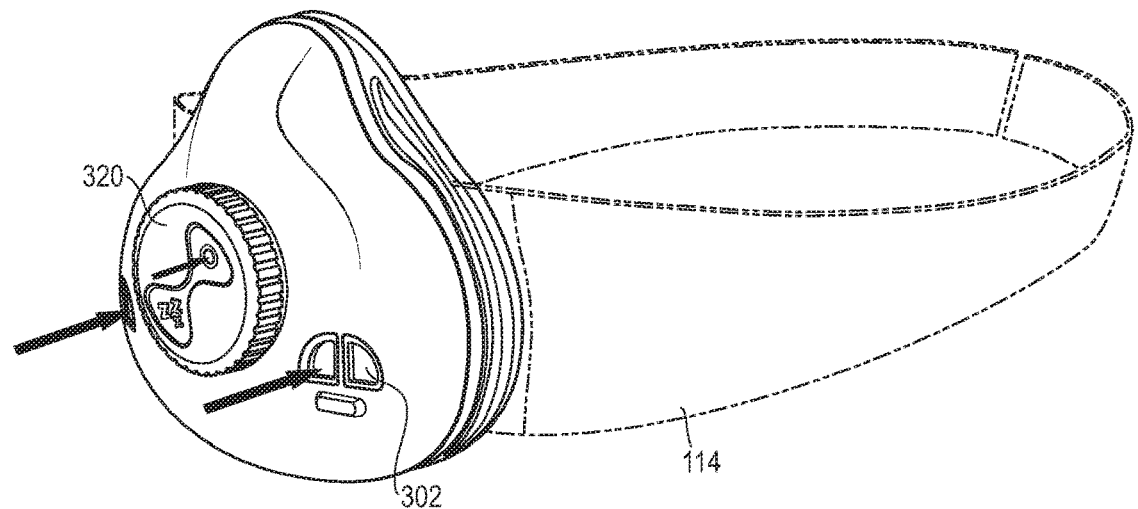
FIGS. 42A and B are isometric views of the device shown in FIGS. 40A-D during inhalation and exhalation respectively.
Figure 42B:
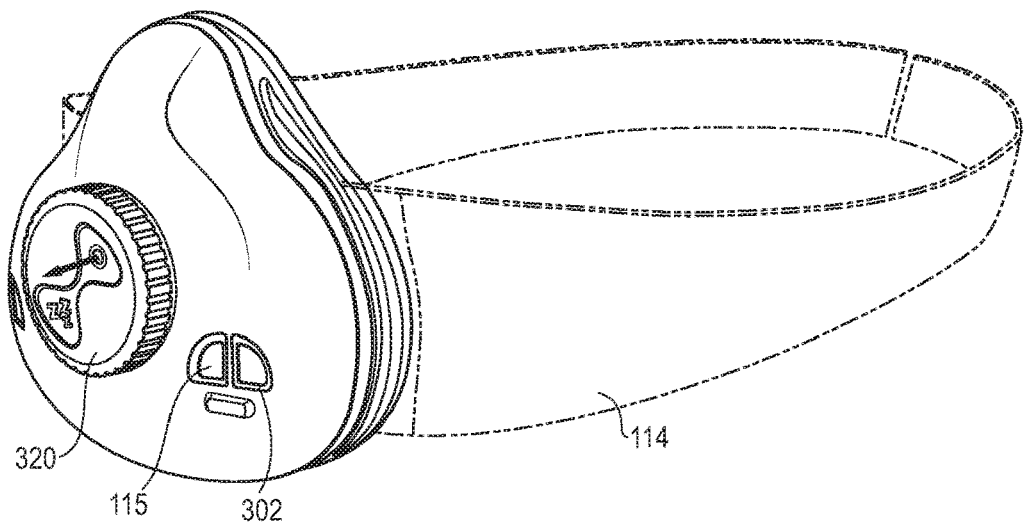

Referring to FIGS. 40A-D, one embodiment of a PEP device covers both the nose and the mouth of the user, providing resistance on exhalation regardless of the breathing pathway. The device is configured as a mask 113 having a body that seals on the face of the user via a sealing surface 112. The mask is secured to a user's face via a band 114 made of a comfortable, breathable material such as wool, bamboo, tencel, cotton, nylon, polyester, Gore-Tex, etc., or a non-breathable, flexible material such as neoprene. The mask 113 has three ports. Two ports 302 house two inhalation valves 115 and one port 304 houses an exhalation dial 116, having a first fixed member with two openings and a second rotatable member having an hourglass dial opening 330, with an first upper lobe opening 322 that overlies one of the two openings 117, 118, and a second lower lobe opening 324 that overlies one of two indicia 326, 328, shown as sleeping indicia (e.g., "Z"s) and activity indicia (e.g. shoes). As shown in FIG. 40B, first and second openings are shown, with one of the openings being covered by a dial. The exhalation dial 116 has two settings, shown in FIG. 41, which exposes or aligns the first lobe with either a small hole 117 or a large hole 118, with the holes having different cross-sectional areas. The small hole is to accommodate tidal breathing during sleep and the large hole is to accommodate breathing patterns typical of exercise, with both hole sizes yielding an exhalation pressure between 1-15 cmH2O, preferably between 5-10 cmH2O and most preferably between 5-10 cmH2O. The sizing of the holes is to accommodate a relatively equivalent exhalation pressure for both sleeping and activity. As flow rates are typically higher during activity, the hole is larger to decrease the resistance and stabilize pressures. In other embodiments, the ability to adjust settings may or may not be present. The inhalation valves 115 open during inhalation to accommodate negligible resistance to inhalation as shown in FIG. 41A, and close during exhalation as shown in FIG. 41B. Flow may occur through the exhalation dial 116 during inhalation, but the majority of flow will be through the opened inhalation valves 115. During exhalation, flow is restricted to only the small hole 117 or large hole 118, depending on the dial setting chosen by the user. To change settings, the exhalation dial 116 may be rotated upon its central axis to open and close the respective holes by aligning the first lobe with one or the other of the holes. In other embodiments, settings may be changed by a sliding member, interchangeable part, electronic setting control, or other method of adjusting the hole (orifice) size. The band 114 may be secured around the user's head elastically, with a Velcro section, an adjustable strap, or other obvious methods of securing the device around one's head or ears. In addition to providing positive exhalation pressure, deadspace may be incorporated in the mask 113 to increase CO2 and further improve breathing control. The deadspace and/or a filter material may be incorporated in the mask 113 to add heat and moisture exchange (HME) capabilities and improve the quality of inhaled air by warming it and utilizing moisture from exhaled breath.

The body of the mask is shaped to cover one or both of the user's mouth and nose. The dial is moveably mounted to the body and is moveable between at least first and second positions. The dial opening is aligned with the first opening when the dial is in the first position, and the dial opening is aligned with the second opening when the dial is in the second position. Conversely, the second opening is covered by the dial when the dial is in the first position, and the first opening is covered by the dial when the dial is in the second position. The viewing opening is aligned with first indicia when the dial is in the first position and the viewing opening is aligned with second indicia when the dial is in the second position. The first indicia are instructive about breathing patterns associated with the first opening and the second indicia are instructive about breathing patterns associated with the second opening.

Figure 48:
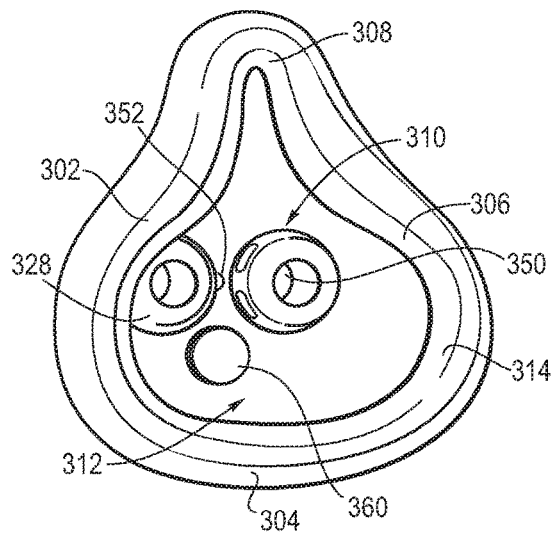
FIG. 48 is a rear perspective view of the mask embodiment shown in FIG. 47.
Figure 49:
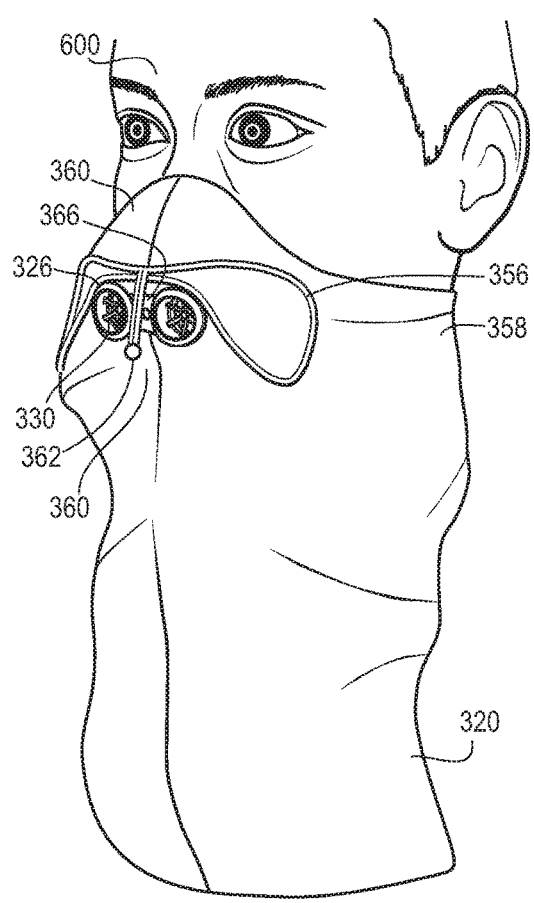
FIG. 49 is a front perspective view of the mask embodiment shown in FIG. 47 with a neck tube applied thereto.
Figure 50:
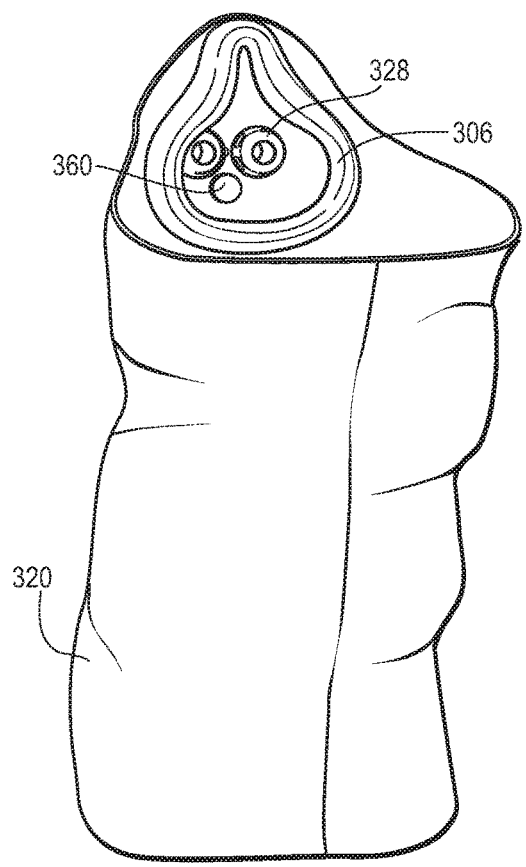
FIG. 50 is a rear perspective view of the mask embodiment shown in FIG. 48 with a neck tube applied thereto.
Figure 51:
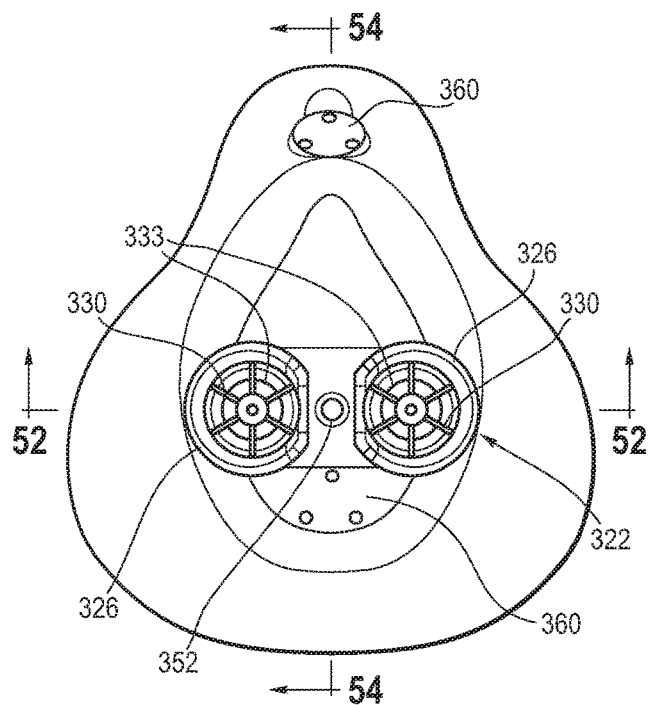
FIG. 51 is a front view of the mask embodiment shown in FIG. 47.
Figure 54:
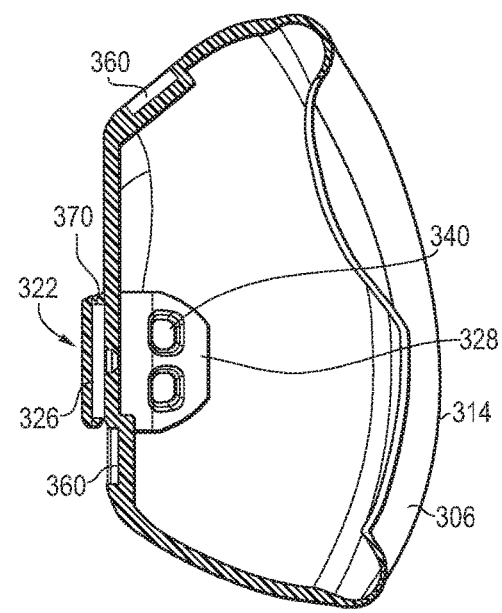
FIG. 54 is a cross-sectional view of the mask embodiment shown in FIG. 51 taken along line 54-54.
Figure 52:
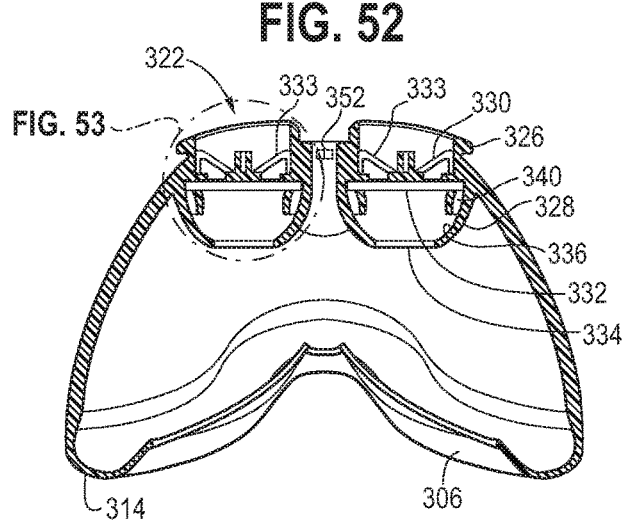
FIG. 52 is a cross-sectional view of the mask embodiment shown in FIG. 51 taken along line 52-52.
Figure 53:
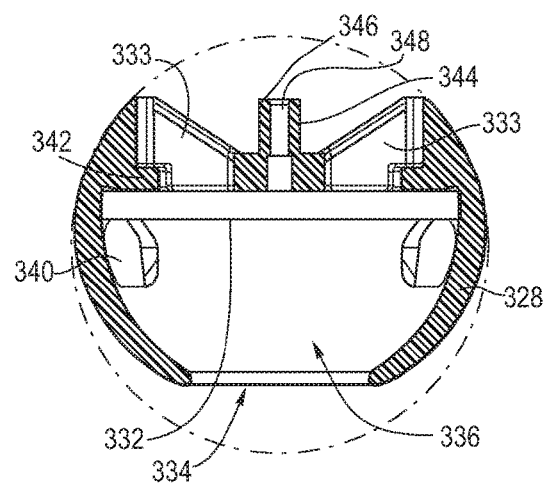
FIG. 53 is enlarged view of a portion of the mask embodiment shown in FIG. 51 taken along detail line 53.

Referring to FIGS. 47, 48 and 51-58, a mask 300 is configured to seal on the face of the user 600 and cover both the mouth and nose. As shown in FIGS. 48, 50 and 54, the mask includes a flexible sealing edge 302, formed by an inwardly curved lip of the mask. In one embodiment, the mask may be made of silicone rubber. The sealing edge forms a generally triangular shaped, or tear-drop shaped, opening 310, with curved sides. The opening has a curvilinear bottom edge 304, and curvilinear side edges 306 extending from the bottom edge and meeting at an apex 308. The apex fits over the top of the user's nose, with the user's mouth and nose communicating with the interior space of a cavity 312 defined by the mask.

The mask is intended to be worn while sleeping at altitude to combat AMS and minimize periodic breathing associated with altitude. The mask may also be worn during exercise or rest at altitude to combat AMS. The device seals on a user's face via a sealing surface 314 defined by the sealing edge 302 of the mask 300. The mask provides positive exhalation/expiratory pressure (PEP) to increase the pressure gradient in the airways, thereby increasing oxygen saturation levels and decreasing the severity of hypoxia. The device improves upon limitations associated with current methods for preventing acute mountain sickness (AMS), which may include but are not limited to side effects associated with pharmaceuticals, increased time spent at incremental altitudes (slower ascent profiles), resources spent prior to travel to acclimatize in simulated environment, lack of evidence to support effectiveness, lack of portability and supply of supplemental oxygen, technique and thought required to practice pursed lip breathing and requirement to minimize exertion. For applications where oxygen saturation levels are decreased, the disclosed device improves portability, effectiveness and efficiencies to decrease hypoxia.

The mask may secured to a user's face via a neck tube 320, or shroud, made of a comfortable, breathable material such as wool, bamboo, tencel, nylon, polyester, Gore-Tex, etc. with moisture wicking properties and a resistance to odor. The neck tube 320 may be interchangeable with various fabrics to accommodate different climates or environments. In one embodiment, the neck tube has a continuous periphery so as to define a tubular structure with openings at each end thereof. The neck tube is installed by passing the tube over the user's head until the neck tube surrounds the user's neck and/or head. In other embodiments, the neck tube may have a reclosable fastener, such as a zipper, snaps, Velcro, etc., allowing the tube to be opened along a portion or the entirety of the length thereof, for example to apply the tube around the neck of the user, whereinafter it may be secured by closing the reclosable fastener(s) to form a tube.

In one embodiment, the mask 302 is removable from the neck tube 320, such that the neck tube 320 can be worn without the mask, for example during the day to protect the user from environmental and outdoor elements. The mask also is removably securable to the neck tube 320 so that the neck tube 320 can be worn by itself when therapy is not desired.

The mask 300, shown in FIGS. 47-58, has two ports 322 that house two inhalation valves 324. The ports 322 are each defined by a raised rim portion 326 (mushroom lip) on the exterior of the mask, and a protective dome 328, having a central opening 334, extending from an interior of the mask into the interior space of the cavity. A plurality of openings 361 or windows (shown as four) are formed in the wall defining the dome. The windows allow air flow during inhalation and thereby help minimize inhalation resistance. The ports 322 each define a through opening 336 communicating between the interior space and the ambient environment. A protective grid 330 extends across the through opening so as to prevent the inhalation valve from being tampered with or removed. The grid 330 includes a back plate 332 that may be snapped into the mask, for example over an annular flange 342 formed in the through opening of the mask In other embodiments, the grid is integrally formed with the body of the mask and dome. The back plate has openings 345 defining an inhalation path and defines a sealing surface 343 for the inhalation valve on exhalation. The grid includes a central hub 344 having a through opening 348. The grid includes spokes 333 that define the openings 345 therebetween, and with the spokes being tapered outwardly so as to be thicker adjacent the outer periphery of the openings than adjacent the center of the openings. In one embodiment, the inhalation valve 350 is a center post valve having a center post 351 that may be inserted through the opening 348 in the hub, with an enlarged end portion 353 then engaging the end 346 of the hub. The inhalation valve is disposed in a cavity defined by the protective dome and moves away from the back plate during inhalation as shown in FIGS. 56B and 57B, while sealing against the sealing surface of the back plate during exhalation as shown in FIGS. 56A and 57A. In one embodiment, the valve is configured as an umbrella valve, while in other embodiments, the valve may be configured as a flap, diaphragm, duckbill or other known types of valves. The size of the opening(s) defining the inhalation path are sufficient to provide substantially unrestricted inhalation.

Figure 56A:
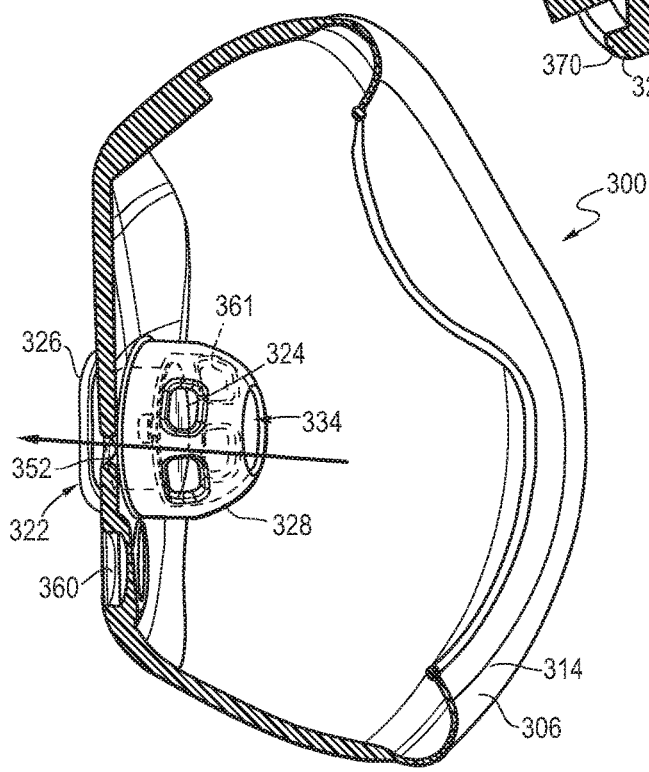
FIGS. 56A and B show a cross-section of the mask during exhalation and inhalation respectively.
Figure 56B:
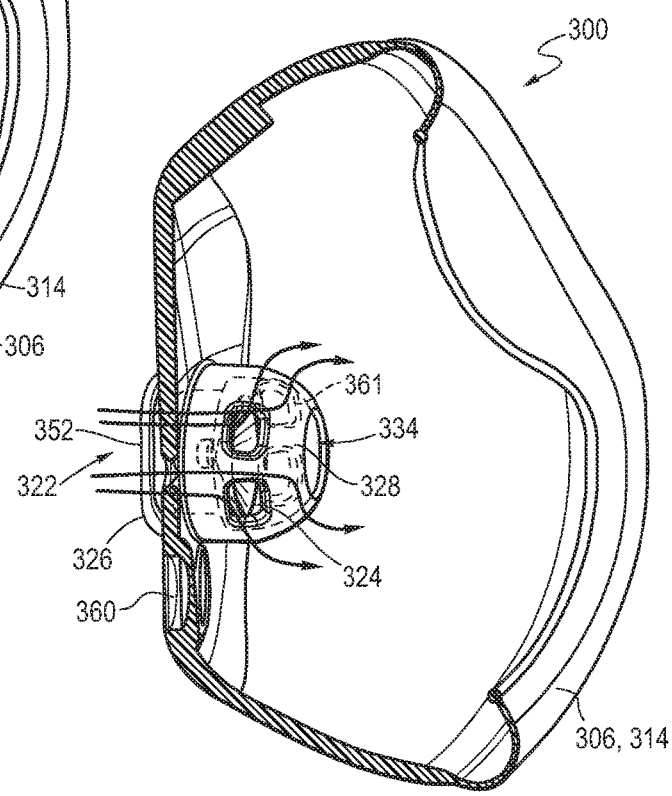
Figure 57A:
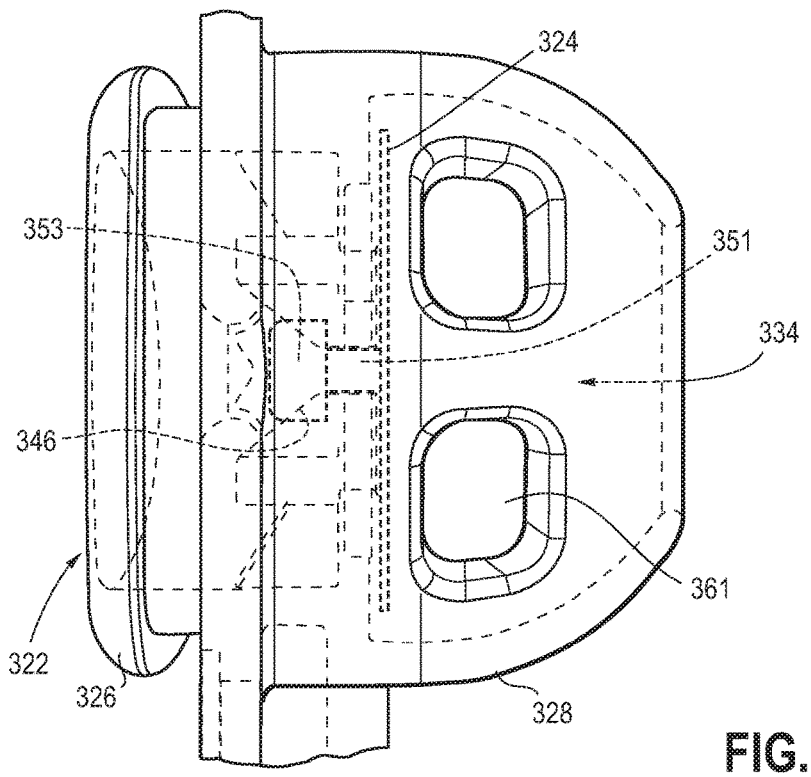
FIGS. 57A and B are enlarged cross-sectional views of the mask during exhalation and inhalation respectively.
Figure 57B:
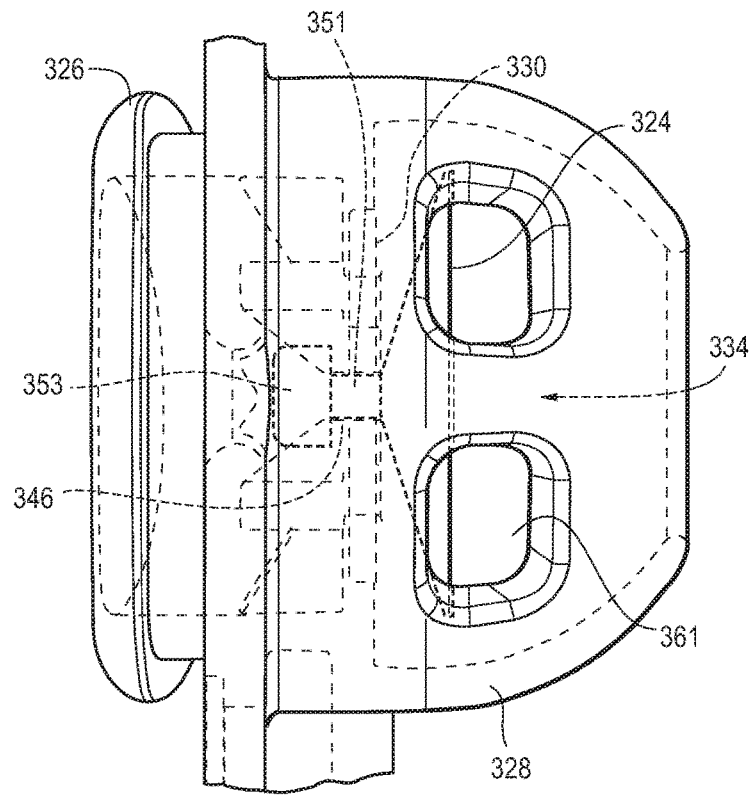

During inhalation, air may also pass through the exhalation orifice 352 as shown in FIG. 56B.

A third port defines the exhalation orifice 352. The size of the exhalation orifice 352 creates the positive exhalation pressure and may be achieved with one orifice or a plurality of orifices. In an embodiment with a single exhalation orifice 352, the diameter of the exhalation orifice 352 is between 2 mm and 10 mm (area between 3.142 mm$^2$ and 78.540 mm$^2$), preferably between 2 mm and 5 mm (area between 3.142 mm$^2$ and 19.635 mm$^2$) and most preferably between 3 mm and 4 mm (area between 7.069 mm$^2$ and 12.566 mm$^2$). It should be understood that the exhalation orifice may have other non-circular shapes, but with the area of the opening being within the noted ranges. Likewise, it should be understood that a plurality (more than one) of exhalation orifices may also be provide, with the cumulative areas of the orifices being within the noted ranges. The size of the orifice(s) are designed to yield an exhalation pressure between 1-15 cmH2O, preferably between 5-10 cmH2O and most preferably between 8-10 cmH2O at a constant flow of 20 L/min. It should be understood that in one embodiment, the exhalation orifice is not covered or blocked by any member, including a valve or other flow control member, but rather remains open during all phases of inhalation and exhalation. In other embodiments, the orifice may be fitted with a filter, which permits two-way flow, or a valve that permits only an exhalation flow.

The inhalation valves 330 open during inhalation to provide negligible resistance to inhalation, and close during exhalation. Flow may occur through the exhalation orifice 352 during inhalation, but most of the flow will be through the inhalation openings exposed by the opened inhalation valves 350. The exhalation orifice and inhalation openings 345, as well as the dome openings 334, 361 and overall through openings 336 of the ports, define the inhalation path. Valving used for the inhalation valves 350 may be any of the valves previously disclosed, with umbrella valves utilized in one embodiment. During exhalation, flow is restricted to only the exhalation orifice 352, which defines an exhalation path. In other embodiments, various sizes of exhalation orifices 352 may be included to create various settings. These settings may be changed by a rotary dial, sliding member, interchangeable part, electronic setting control, or other method of adjusting the size of the orifice(s), as shown above with respect to other embodiments.

The neck tube 320 is elastically secured around the user's head and/or neck with an elastic band, which may be adjusted with a drawstring mechanism 356 to customize the fit. In other embodiments, the neck tube fabric may be integrally configured with elastic properties, such as mechanical stretch exhibited for example by polyester or other similar materials, or additive stretch exhibited for example by spandex or similar materials. In other embodiments, the neck tube may have integral elastic properties, in combination with a separate elastic member, such as a band, and/or drawstring. In one embodiment, the drawstring adjustment mechanism 356 includes a cord 358 and cord lock 362. To prevent barotrauma and minimize discomfort during heavy breathing, coughing, or as a safety feature if the exhalation orifice(s) 352 is/are blocked, the sealing surface 314 will lift off the user's face and effectively break the seal below 25 cmH2O, and preferably below 20 cmH2O, while in other embodiments, the seal will be broken between 20 cmH2O and 25 cmH2O, or between 23 cmH2O and 25 cmH2O.

To secure and create a seal on the user's face, the neck tube 320 tightens using a drawstring mechanism, including the cord 358, cord end 359, cord lock 362 and cord loops 363. The cord 358 is secured to the neck tube by multiple cord loops 363, which create tension points as the mechanism is tightened by pulling on the cords downstream of the cord lock, or by pulling on the cord end 359. The cord lock 362 is used to secure the cord 358 such that once the desired tightness is achieved, the neck tube 320 stays secure. A cord end 359 may be used to secure the two ends of the cord 358 as well as act as a holding point for the user to pull on the cord 358 when tightening the cord by drawing the cord through the loops 363.

The drawstring mechanism is aligned with the front, center of the mask, creating tension in the neck tube 320 directly over the mask and effectively creating a seal on the user's face. An additional benefit of the drawstring mechanism in front of the user's face is the ease of use due to the ability to see and feel the mechanism in front of the face and it does not create a pressure point on a surface of the head that the user will likely be sleeping on (i.e. either side of the head or the back of the head). In other embodiments, they drawstring mechanism may be on the side or back of the neck tube and may be replaced with an alternative tightening mechanism such as hook and loop (i.e. Velcro®), button holes, a clasp mechanism, etc.

Figure 58:
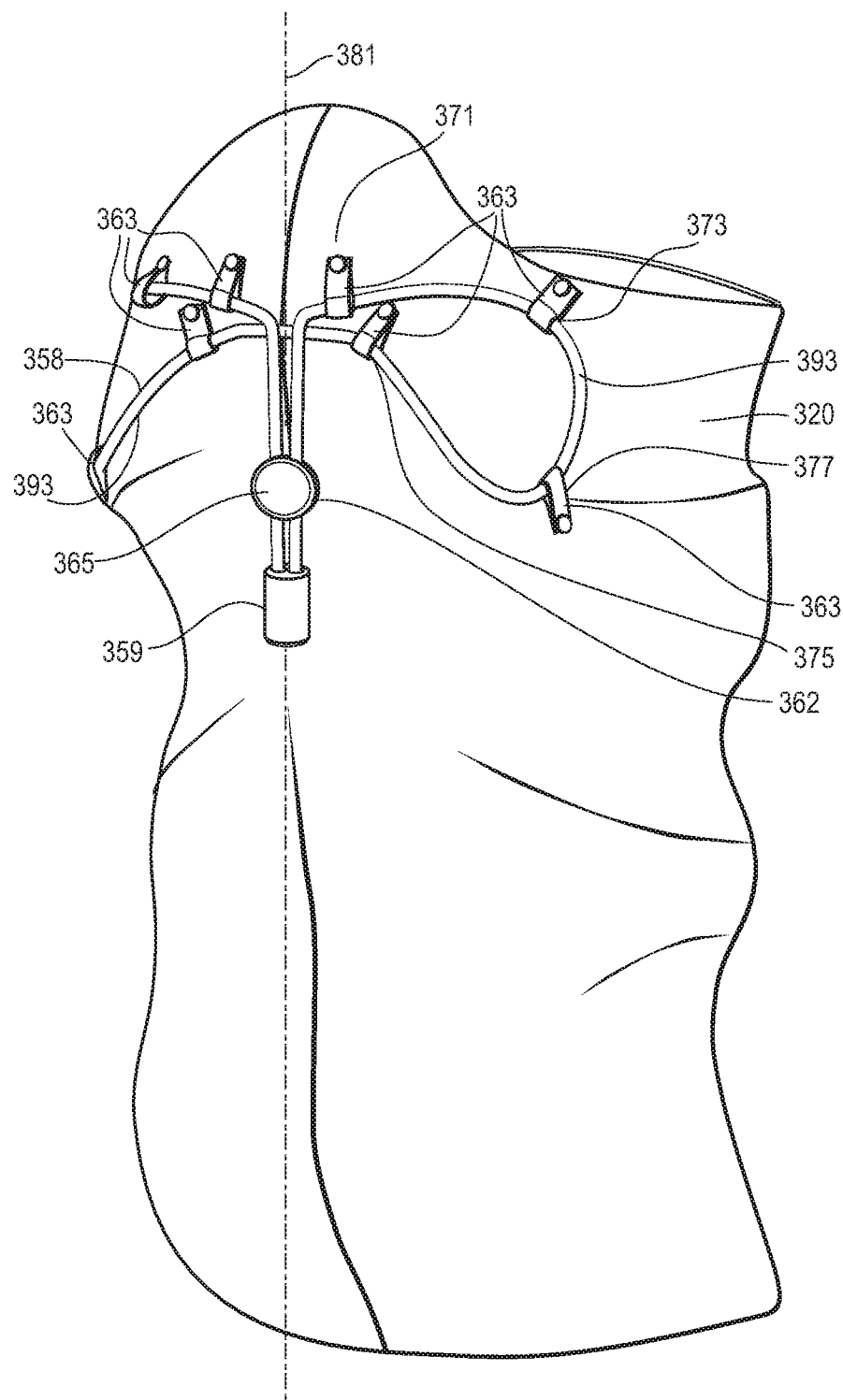
FIG. 58 is a front perspective view of a mask embodiment shown in FIG. 47 with a neck tube applied thereto.

The number of cord loops 363 may be between 2-11, preferably between 5-9. The cord 358 is preferably non-elastic but may have elastic properties in an alternative embodiment. Referring to FIG. 58, the cord loops are coupled to the neck tube, for example by sewing, adhesives, snaps, or other suitable components, and are disposed on an exterior surface thereof. Each loop may have a fixed end fixed to the neck tube, with an opposite loop free end not being attached. The loops are arranged such that a tensile force is applied by the cord against the loop free end, putting the loop in tension against the anchored fixed end. For example, on each side of a vertically extending centerline, a first upper loop 371 is disposed inboard on one side of the centerline 381 and has a free end extending downwardly from the fixed end. A second upper loop 373 is spaced outboard from the first upper loop and has a free end extending downwardly and slightly inwardly from the fixed end thereof. A first lower loop 375 is spaced downwardly and slightly outboard of the first upper loop, with a free end extending downwardly from a fixed end. A second loop 377 is spaced outwardly from the first lower loop and downwardly from the second upper loop, but with a free end extending upwardly from a fixed end. The cord is threaded through the loops to form a bow-tie shape, with a left and right cord loop 393. Specifically, the cord extends upwardly from opposite free ends (which may be captured by the cord end 359) along the centerline 381. One cord length passes to the left side, while the other cord length passes to the right, both through a corresponding first upper loop, then through the second upper loop, the second lower loop and finally the first lower loop where they are joined as the cross the centerline between the first lower loops. Pulling on the cord end creates tension in the cord as it pulls the loops and shortens the cord loop 393 formed on each side of the mask.

The cord lock 362 is made of plastic and may or may not have a metal spring that rests in tension and compresses when the button 365 on the cord lock 362 is pressed to slide the cord 358 and tighten or loosen the neck tube 320. The surface area of the button 365 is between 50-500 mm$^2$, preferably between 100-150 mm$^2$, allowing for ease of use when dexterity is compromised (i.e. from the cold or from wearing gloves).

Figure 55:
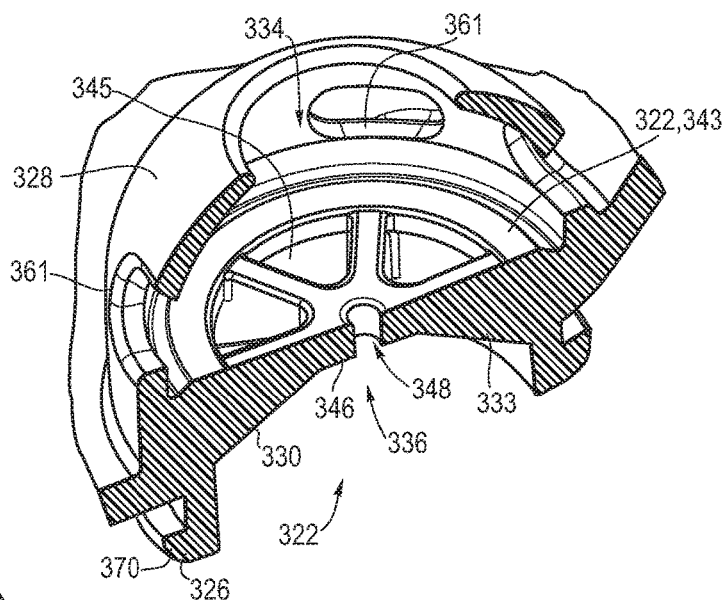
FIG. 55 is a partial cut-away review of a portion of the mask embodiment.

In the embodiment shown in FIG. 47-54, the mask 300 attaches to the neck tube 320 via one or more magnets 360, or other releasable fasteners. A positioning hole 366 in the neck tube 320 aligns with the raised rim portions 326, which are undercut as shown in FIGS. 54 and 55 so as provide a lip feature 370 that function as fabric catches on the mask 300 so as to align and locate the mask such that the user is not breathing through the fabric of the neck tube, or such that the fabric is prevented from covering the ports and interfering with the inhalation and exhalation paths. The catches also help hold the neck tube on the mask. One or a plurality of magnets may also be used to properly position and secure the mask 300 in the neck tube 320. In one embodiment, magnets 360, or a magnetically attractive receiver, such as ferromagnetic material (e.g., metal plate), are in-molded in the mask at upper and lower locations, for example adjacent the apex and below the inhalation valves across from the user's mouth. Mating magnets, or ferromagnetic materials, are likewise sewn into, or attached to the neck tube 320. Exemplary suitable magnets are shown in Table 1, with Applied Magnets also offering a suitable magnet meeting the C specification of Table 1.

TABLE 1

MAGNET SPECIFICATIONS

| | -A | -B | -C |
|---|---|---|---|
| MANUFACTURER | K&J MAGNETICS | K&J MAGNETICS | DURA MAGNETICS |
| DIAMETER | 9.53 (3/8") | 9.53 (3/8") | 9.53 (3/8") |
| THICKNESS | 1.59 (1/16") | 1.59 (1/16") | 3.18 (1/8") |
| MATERIAL | Nd Ni-PLATED | Nd Ni-PLATED | SmCo |
| GRADE | N45SH | N42SH | 26MGOe |

Alternatively, other fastening mechanisms such as traditional hook and loop (i.e. Velcro®), silicone "key and hole" (abbreviation of hook and loop), buttons, zippers or a press fit mechanism may be used to secure the mask 300 to the neck tube 320. In a similar embodiment, the neck tube 320 may be free of a positioning hole, and the neck tube 320 covers the entire mask 300, allowing the user to breathe through the fabric.

In addition to providing positive exhalation pressure, dead space is incorporated in, or created by the interior space of, the mask 300 to increase CO2 and reduce periodic breathing while sleeping. The amount of dead space is between 50 mL and 500 mL, preferably between 50 mL and 200 mL and most preferably between 100 mL and 150 mL.

The dead space incorporated in the mask 300 and properties of the neck tube 320 fabric covering the inhalation and exhalation ports (if applicable in the given embodiment) add heat and moisture exchange (HME) capabilities and improve the quality of inhaled air by warming it and utilizing moisture from exhaled breath. This further helps with coughing, sore throat and congestion caused by exposure to high altitude environments. When not in use, the mask 300 or both the mask 300 and neck tube 320 may be stored in a conformable carrying case.

Due to the nature and environment for use, the material of the mask is preferably comfortable for the user to wear in, on and/or over the nose, mouth or both for extended periods of time. In the preferred embodiment, components involved in sealing or contacting the oral or nasal passage are made from a flexible material such as silicone, TPU, polyurethane, neoprene or polyisoprene, or an easily formable material such as polyurethane foam, ethyl vinyl acetate (EVA) or acrylic. In one embodiment, the disposable portion of the device may be completely biodegradable to allow for friendly disposal in high altitude environments where waste is a growing concern. In embodiments with integrated electronics, parts must be sealed to withstand the harsh weather associated with high altitudes, i.e. encapsulation, ultrasonic welding or potting with a material designed to withstand and protect electronic components from extreme high/low temperatures, moisture, and shock. In embodiments including a neck tube or neck warmer, the material is lightweight, breathable, moisture wicking, odor resistant and quick-drying.

It should be understood that the mask may be used without the neck tube in some embodiments, with straps, ear loops or one or more bands being used to secure the mask to the user.

Figure 43:
FIG. 43 is a schematic showing the connected relationship, or drawings continuation, of the flow chart depicted in FIGS. 43A and B.
Figure 43A:
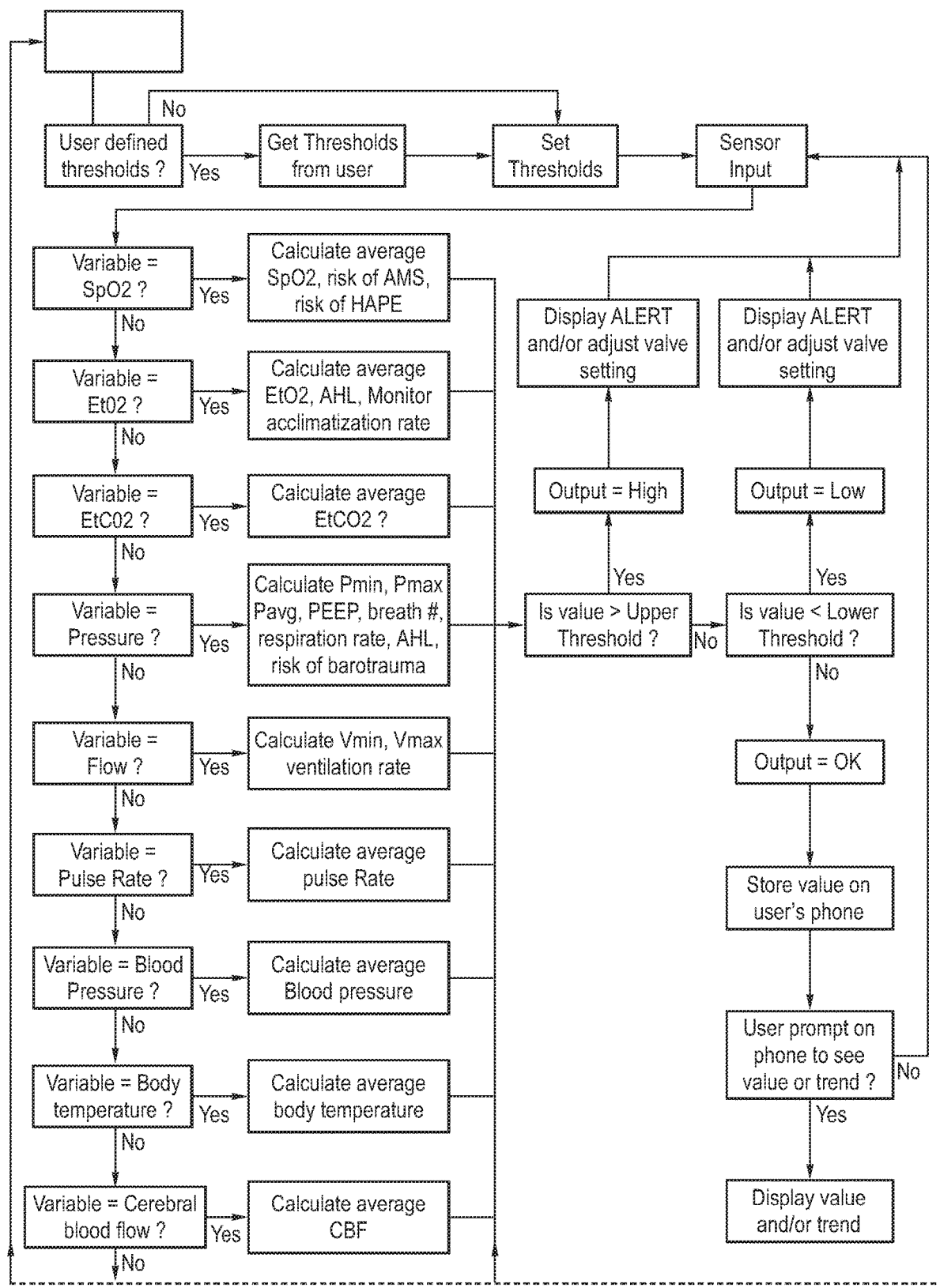
FIGS. 43A and B show a flow chart for the operation of another embodiment of a device.

FIG. 43, and FIGS. 43A and B, disclose an algorithm for an embodiment that utilizes sensors and an electronic circuit for monitoring. In this embodiment, the feedback from the sensors may control the valve configuration to achieve various pressure settings. In other embodiments, feedback may be solely in the form of alerts to the user or accessible data for later review. The electronic module 119 is located in the flow path of the device, and may be incorporated in any of the previously disclosed embodiments.

Figure 43B:
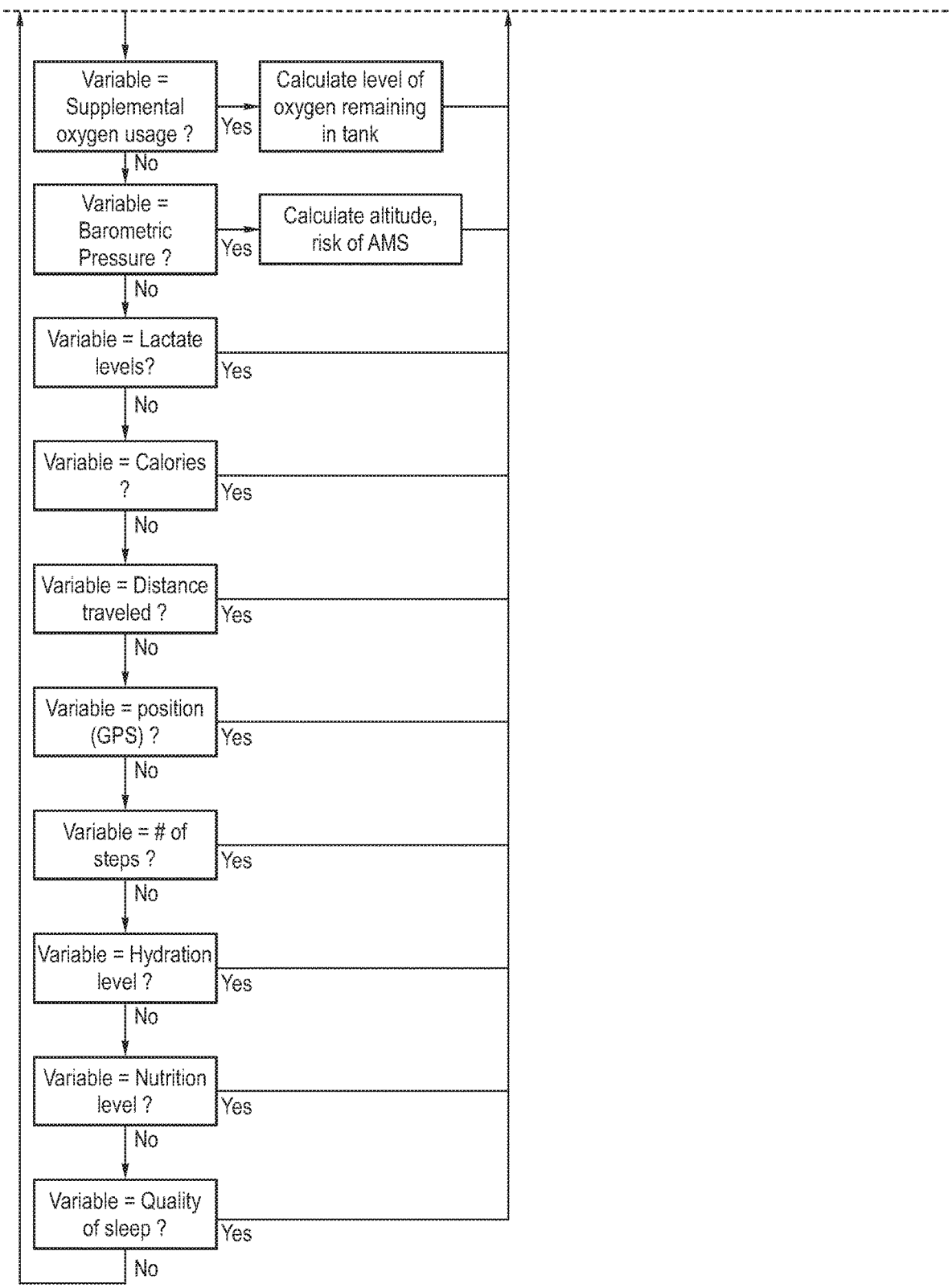
Figure 44:
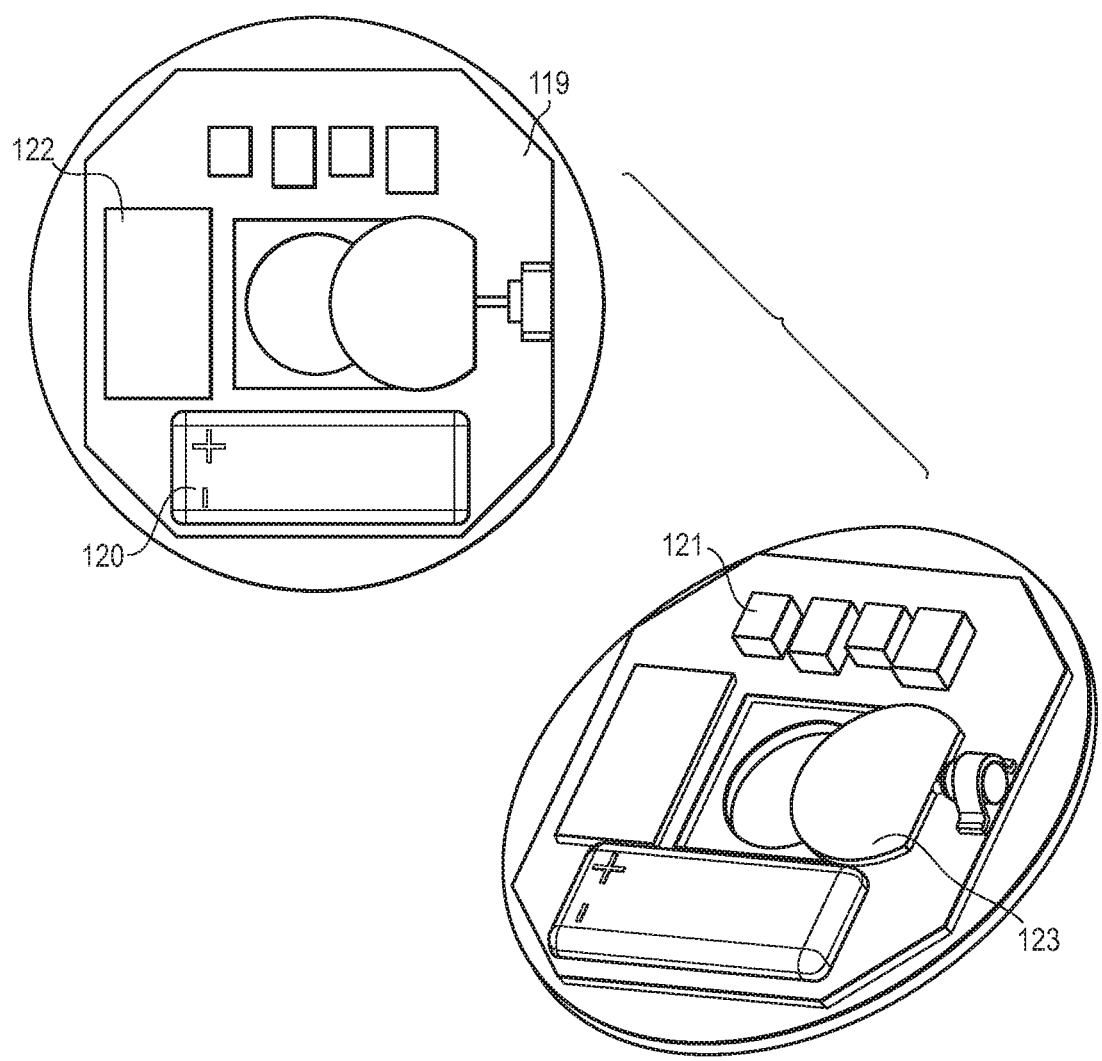
FIG. 44 is a top and isometric views of another embodiment of a device.
Figure 47:
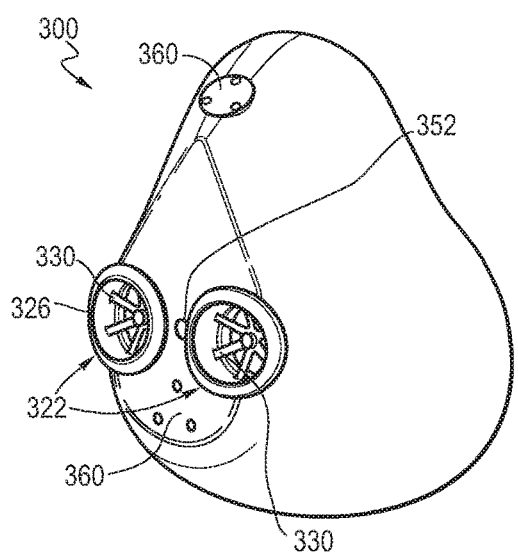
FIG. 47 is a front perspective view of a mask embodiment.

FIG. 44 shows an exemplary embodiment of the electronic module 119. Sensors 120 in the electronic module may include but are not limited to those capable of measuring oxygen saturation levels (pulse oximeter, such as the commercially available MAX30100 sensor from Maxim Integrated), respiration rate (pressure sensor, flow sensor, position sensor, or combination thereof), inhalation and exhalation pressure (pressure sensor), inhalation/exhalation flow (differential pressure flow sensor, flow sensor, turbine flow sensor, electromagnetic flow sensor, thermal mass flow sensor, velocity flow sensor, mass flow sensor, venturi tube, rotameter, pitot tube, ultrasonic doppler flowmeter, positive displacement flowmeter, or combination thereof), pulse rate (commercially available sensor such as the MAX30100 from Maxim Integrated, or LED and detector at desired wavelength), blood pressure (ultrasonic doppler or pulse wave velocity), temperature (thermocouple, thermistor, semiconductor-based temperature sensor or resistance temperature detector), number of steps (accelerometer or commercially available pedometer such as MMA9553L from NXP), calories, distance traveled (GPS, altimeter), position (GPS, accelerometer, gyroscope), altitude (barometric pressure sensor), hydration level (capacitor for measuring skin impedance, moisture sensor for sweat measurements, etc.), nutrition level (spectrometer), quality of sleep (pressure sensor, flow sensor, position sensor, accelerometer, or combination thereof), blood lactate levels (LED and detector), supplemental oxygen usage (oxygen sensor, flow sensor, or combination thereof), cerebral blood flow (blood flow sensor, such as those commercially available from Kyocera Corporation), $EtCO_2$ (commercially available capnograph such as those available from COZIR, or LED and detector), $EtO_2$ (oxygen sensor) and breathing sounds (microphone). For variables referring to blood characteristics, a portion of the electronic module 119 is in contact with the skin or mucous membrane in an area such as the nose, where blood circulation is abundant. The electronic module 119 may be powered with a battery 120 that is disposable or rechargeable via the grid, solar, wind, sweat, the user's breath, or any other sustainable energy source. The electronic module 119 is connected to a user's phone via Bluetooth or Wi-Fi in a preferred embodiment, but may also be connected to another handheld device with computing capabilities in other embodiments. The electronic module 119 may be turned on by the user prior to use, or may incorporate sensors to wake up the control unit when the device is properly secured on the user. The electronic module 119 may be a standalone component which can be purchased separately and inserted into previously disclosed embodiments to create an upgraded version of the device with monitoring capabilities, or may be fitted with an adapter to hook up directly to an already existing oxygen mask, scarf, sleeping bag, or hood of a jacket. Alternatively, the electronic module 119 may be fully integrated in any of the previously disclosed embodiments with modifications to the valving system to accommodate differences for various embodiments. The algorithm in FIGS. 43, 43A and 43B show the loop that starts once the power is on. Upon startup, a variable is selected, with variables being the data stored from the sensors 121. Once the variables are set, thresholds are applied automatically, or may be overridden by input from the user if they wish to customize the thresholds. Data is captured from sensors 121 and various calculations are made either on the control unit 122 or the user's phone, which serves as a control unit. At least one sensor is capable of measuring one or more body functions and/or parameters, and the control unit is operable to determine at least one threshold based on data collected from the at least one sensor.

FIG. 45 includes a chart that represents thresholds for various calculations included in the algorithm. For oxygen saturation levels (SpO2), the average value is obtained for the user's reference as well as the risk of AMS and NAPE. For risk of AMS, these values are based on a decrease of 4.9% within 30 mins or compared to the average at that altitude, as shown in FIG. 46. For risk of NAPE, these values are based on a decrease of 10-20% compared to the average at that altitude. For end-tidal oxygen (EtO2), the average value is obtained for the user's reference. In combination with the end-tidal carbon dioxide (EtCO2), the EtO2 may provide insight into breathing patterns and change over time. For EtCO2, the average value is obtained for the user's reference and the arterial partial pressure of carbon dioxide (PaCO2) is estimated for feedback on acclimatization based on average values at a given altitude. The Apnea-Hypopnea Index (AHI) is also calculated while the user is sleeping, and greater than 5 apneas/hr is indicative of the threshold. Pressure values are used to determine the risk of barotrauma (if pressure during exhalation is greater than 10 cmH2O) as well as aid in calculating the AHI. They may also be used to determine the respiration rate. For flow, the minute ventilation, alveolar ventilation and respiratory rate are calculated to determine if the user's breathing patterns are optimized for acclimatizing at high altitude, encouraging slow, deep breaths. The pulse rate is monitored to calculate the average and determine if it is approaching or above the individual's maximum heart rate, often calculated by subtracting one's age from the value of 220. With blood pressure, the average is monitored to determine if values go outside of the recommended range of less than 120 mmHg (systolic) and 80 mmHg (diastolic). For body temperature, the average is monitored to determine if values are outside of the normal range and if the user is approaching hypothermia (<35° C. or 95° F.), fever or hyperthermia (>37.5° C. or 99.5° F.), or hyperpyrexia (>40° C. or 104° F.). Cerebral blood flow (CBF) averages may be used to provide indication of the level of acclimatization, as CBF peaks within 2-3 days at altitude and returns to near sea level in 1-3 weeks.

The device may be connected to a user's oxygen tank to further improve oxygenation at altitude, and a dedicated sensor may monitor its usage to alert the user when the tank is getting low (i.e. <10% remaining). Barometric pressure is used to calculate the altitude for the user's reference as well as to relay the risk/incidence of AMS at the given altitude or if the person ascends more than 500 m in a given day.

Barometric pressure may also be used to determine the time that the user spends at a given altitude, which may aid in determining the cause of symptoms, which should not be attributed to AMS if they onset after 3 days at altitude. A list of various altitudes and average values for barometric pressure, PaO2, SaO2 and PaCO2 is shown in FIG. 46. Variables such as lactic acid levels, calories, distance traveled, GPS, number of steps, hydration level, nutrition level, and quality of sleep are mainly for the user's reference, though user-defined thresholds may be applied to reach desired goals or accommodate individual needs. If the upper end of the threshold for a given variable is reached, an alert will be sent to the user's phone to warn them that they have gone above of the recommended value range. If the lower end of the threshold for a given variable is reached, an alert will be sent to the user's phone to warn them that they have gone below the recommended value range. If either the upper or lower threshold are reached, the electronic module 119 may also change the resistance setting of the device without requiring user input to optimize breathing and aid in returning the value to the recommended range. The depicted embodiment achieves this by an electronically actuated valve 123. The valve 123 is reconfigurable in response to the at least one threshold determined by the control unit. For example, the valve 123 may be actuated (e.g., moved, stiffened or relaxed) to provide more or less resistance based on the determined thresholds. Values for all variables are stored on the user's phone and can be accessed individually or displayed as a trend over a given period of time. Data may also be shared with guides or physicians when values are lower/higher than the norms or as the user desires.

Due to the interface of the device(s) with the user's oral and nasal cavities, the material of the device must be comfortable for the user to wear in the nose, mouth or both for extended periods of time. In one embodiment, components involved in sealing or contacting the oral or nasal passage are made from a flexible material such as silicone, TPU, polyurethane, neoprene or polyisoprene, or an easily formable material such as polyurethane foam, ethyl vinyl acetate (EVA) or acrylic. In one embodiment, the disposable portion of the device may be completely biodegradable to allow for friendly disposal in high altitude environments where waste is a growing concern. In embodiments with integrated electronics, parts must be sealed to withstand the harsh weather associated with high altitudes, i.e., encapsulation, ultrasonic welding or potting with a material designed to withstand and protect electronic components from extreme high/low temperatures, moisture, and shock. The various positive airway pressure devices can be used for individuals not acclimatized to altitude to improve oxygen saturation levels and decrease the risk of AMS. Specifically, the user may apply the device at high altitudes, for example when sleeping or when awake, without the need to have performed prior simulation training or use of the device at lower altitudes.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A positive expiratory pressure device comprising:
a mask comprising a body shaped to cover the user's mouth and nose and defining an interior space,
wherein the mask is configured with a first port that communicates directly between an ambient environment surrounding an exterior of the body and the interior space,
wherein the at least one first port is configured with an inhalation valve and wherein the first port defines an inhalation path communicating with the body, and
a second exhalation port sized to produce an exhalation pressure between 1-15 cmH$_2$O, wherein the second exhalation port has an unobstructed orifice with a non-variable and minimal cross-sectional area that communicates directly between the interior space and the ambient environment,
wherein the positive expiratory pressure device is free of any exhalation valves; and
a neck tube coupled to the mask and extending downwardly therefrom.

2. The positive expiratory pressure device of claim 1 wherein the neck tube is releasably coupled to the mask.

3. The positive expiratory pressure device of claim 2 wherein the neck tube is releasably coupled to the mask with a magnet.

4. The positive expiratory pressure device of claim 1 wherein the neck tube does not cover the first inhalation port or the second exhalation port.

5. The positive expiratory pressure device of claim 4 wherein the mask comprises fabric catches for aligning one or more openings in the neck tube with the first inhalation port and the second exhalation port on the mask.

6. The positive expiratory pressure device of claim 1 wherein the neck tube comprises an elastic member configured to engage the user.

7. The positive expiratory pressure device of claim 6 further comprising a drawstring mechanism for adjusting the elastic member.

8. The positive expiratory pressure device of claim 1 wherein the neck tube is the only feature for securing the mask to the user.

9. The positive expiratory pressure device of claim 1 wherein the body defines a dead space external to the user.

10. The positive expiratory pressure device of claim 1 wherein the unobstructed orifice is configured as a single orifice having an area of between 3.142 mm$^2$ and 78.540 mm$^2$.

11. The positive expiratory pressure device of claim 1 comprising an electronic module coupled to the mask, the electronic module comprising at least one sensor capable of measuring one or more body functions and/or parameters, and a control unit operable to determine at least one threshold based on data collected from the at least one sensor.

12. The positive expiratory pressure device of claim 1 wherein the neck tube is open along a portion or an entirety of a length thereof.

13. The positive expiratory pressure device of claim 12 further comprising a fastener closing the open neck tube.

14. The positive expiratory pressure device of claim 1 wherein the neck tube has a continuous periphery defining a tubular structure with openings at each end of the tubular structure.

15. A method of using a positive expiratory pressure device comprising:
positioning a body of a mask to cover a user's mouth and nose, wherein the mask is configured with a first port configured with an inhalation valve and communicating directly with an ambient environment surrounding an exterior of the body, and a second exhalation port comprising an unobstructed orifice with a non-variable and minimal cross-sectional area;
positioning a neck tube around a neck of the user, wherein the neck tube is coupled to the mask and holds the mask on the user;
inhaling only from an ambient environment through the first port and thereby opening the inhalation valve;
exhaling through the unobstructed orifice of the second exhalation port directly to the ambient environment from an interior of the body and creating an exhalation pressure between 1-15 cmH$_2$O; and
wherein the positive expiratory pressure device is free of any exhalation valves.

16. The method of claim 15 further comprising decoupling the mask from the neck tube.

17. The method of claim 16 wherein said decoupling comprises releasing a magnetic force between the mask and neck tube.

18. The method of claim 15 further comprising positioning the neck tube on the user without the mask being positioned on the user.

19. The method of claim 15 wherein the neck tube does not cover the first inhalation port or the second exhalation port.

20. The method of claim 15 wherein the unobstructed orifice is configured as a single orifice having an area of between 3.142 mm$^2$ and 78.540 mm$^2$.

21. The method of claim 15 wherein the neck tube has a continuous periphery defining a tubular structure with openings at each end of the tubular structure, and wherein positioning the neck tube around the neck of the user comprises passing the user's head through the tubular structure.

22. The method of claim 15 wherein the neck tube is open along a portion or an entirety of a length thereof, and wherein positioning the neck tube around the neck of the user comprises wrapping the open neck tube around the neck of the user.

23. The method of claim 22 further comprising securing the open neck tube around the neck of the user with a fastener.

* * * * *

UNITED STATES PATENT AND TRADEMARK OFFICE
CERTIFICATE OF CORRECTION

| | | |
|---|---|---|
| PATENT NO. | : 11,439,869 B2 | Page 1 of 1 |
| APPLICATION NO. | : 15/983741 | |
| DATED | : September 13, 2022 | |
| INVENTOR(S) | : Costella et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 612 days.

Signed and Sealed this
Eleventh Day of February, 2025

Coke Morgan Stewart
*Acting Director of the United States Patent and Trademark Office*